United States Patent
Kuwabara

(10) Patent No.: US 8,243,881 B2
(45) Date of Patent: Aug. 14, 2012

(54) RADIOGRAPHY DEVICE

(75) Inventor: Shoji Kuwabara, Ibaraki (JP)

(73) Assignee: Shimadzu Corporation, Kyoto (JP)

( * ) Notice: Subject to any disclaimer, the term of this patent is extended or adjusted under 35 U.S.C. 154(b) by 282 days.

(21) Appl. No.: 12/793,070

(22) Filed: Jun. 3, 2010

(65) Prior Publication Data

US 2010/0296628 A1 Nov. 25, 2010

(30) Foreign Application Priority Data

Jan. 25, 2008 (JP) ................................ 2008-014603

(51) Int. Cl.
*H05G 1/64* (2006.01)
(52) U.S. Cl. ...................................................... 378/98.4
(58) Field of Classification Search .................. 378/6, 7, 378/19, 98.4
See application file for complete search history.

(56) References Cited

FOREIGN PATENT DOCUMENTS

JP 2002-257939 A 9/2002

*Primary Examiner* — Courtney Thomas
(74) *Attorney, Agent, or Firm* — McDermott Will & Emery LLP

(57) ABSTRACT

A radiography device that can be applied to even general-purpose scattered radiation removing means, capable of producing appropriate radiation images that are independently of the status of installation of scattered radiation removing means. A pixel specifying portion specifies particular pixels of the various pixels that comprise an x-ray image. An intensity estimating portion estimates the scattered x-ray intensities (scattered radiation intensities) at the particular pixels specified by the pixel specifying portion and/or the direct x-ray intensities (the direct radiation intensities) of the particular pixels. Consequently, it is possible to estimate appropriately the scattered x-ray intensities and/or direct x-ray intensities at the particular pixels in consideration of the status of installation of a grid (scattered radiation removing means).

22 Claims, 7 Drawing Sheets

RADIOGRAPHY DEVICE

CROSS REFERENCE TO RELATED APPLICATION

This application is based on Japanese Patent Application No. 2008-014603 filed Jan. 25, 2008, which is incorporated herein by reference.

FIELD OF THE INVENTION

The present invention relates to a radiography device that is used in, for example, radiographic x-ray equipment and x-ray CT equipment, and the like, and, in particular, relates to a technology for removing scattered radiation.

BACKGROUND OF THE INVENTION

Conventionally, in radiographic x-ray equipment and x-ray computed tomography (CT) for medical use, a grid to remove scattered radiation (scattered radiation removing means) has been used in order to prevent the scattered x-rays (hereinafter termed "scattered radiation") from the test subject from being incident on the x-ray detector. However, even when a grid is used, a false image is formed by the scattered radiation that passes through the grid, and a false image is formed by the absorbing foil that forms the grid. In particular, when a flat panel (two-dimensional) x-ray detector (FPD: Flat-Panel Detector) wherein detecting elements are arranged in a grid (a two-dimensional matrix) is used as the x-ray detector, the false images such as moire fringes that are produced due to the differences in the spacing between the absorbing foil in the grid are produced in addition to those false images from scattered radiation. False image correction is necessary to reduce these false images. Additionally, recently there has been a proposal for a synchronized grid wherein the layout direction is parallel to either the row or column direction of the detecting elements and there is absorbing foil that is disposed at integer multiples of the pixel spacing of the FPD, so that such moire fringes will not be produced, and there is the need for also for a correction method used therewith. (See, for example, Japanese Unexamined Patent Application Publication 2002-257939.)

While, at present, in methods that perform image processing that includes smoothing, and the like, for correcting the moire fringes, there is a tendency to have a reduction in the resolution of the direct x-rays (hereinafter termed the "direct radiation") when there is excessive correction of false images. As a result, the images wherein the direct radiation x-rays have been reduced, wherein the attempt has been made to reduce the false images reliably during the image processing, do not become more clear, and, conversely, when the emphasis is on the resolution of the direct x-rays in an attempt to make the image more clear, then there will be no reduction in the false images during the image processing, in the so-called trade-off between image processing and clarity. Because of this, it is difficult to perform adequate processing on the false images. Furthermore, while there have been a variety of methods proposed as methods for making corrections for the scattered radiation that remains even when a grid is used, there is a problem in that the correction calculations are time-consuming.

The present applicants have already proposed a method for making corrections using a synchronized grid, to correct pixels wherein the direct radiation is blocked by the absorbing foil, to calculate a distribution for the scattering that has been transmitted through the grid from the blocked pixel column or pixel row, to correct the other pixel signals based on that distribution. Additionally in this method there were proposals for, for example, having the distance between the grid and the x-ray detector be an integer multiple of the height of the absorbing foil, radiation emitting means such as an x-ray tube, the establishment of a grid position, and an absorbing foil shaped so as to cause the shadow of the absorbing foil to be contained within a constant pixel column or pixel row.

However:

1. Usually grids other than synchronized grids are used, and when they are used, the method described above, proposed by the present applicants, is inapplicable.

2. No thought has been given to the impact due to misalignment due to a deformation of the absorbing foil from which the grid is structured, even if a synchronized grid is used, or to the misalignment in position or orientation of the grid as a whole that occurs due to the absorbing foil that structures the grid and the rows and columns of the detector not being perfectly parallel.

3. While in the method described above, proposed by the present applicant, the application of the correction is limited to the pixel column or pixel row blocked by the absorbing foil, the direct radiation is attenuated through absorption by the grid structure other than the absorbing foil, for the other pixel columns or pixel rows. Specifically, a grid cover that covers the absorbing foil, and the like is actually formed by carbon fibers or an aluminum plate, so there is absorption by the grid cover. Additionally, when the middle material, disposed between the absorbing foil and through which the x-rays are transmitted, is formed from aluminum or from an organic substance, there is absorption by the intermediate material. Because the absorption and attenuation thereby is not taken into account, it is possible that there will be an error in the evaluation of the estimated direct radiation intensities for all of the pixels, including the blocked pixels.

4. Furthermore, in the method described above, proposed by the present applicant, the distribution of the scattered radiation that is transmitted through the grid is calculated from the blocked pixel columns or pixel rows, and the signals for the other pixels are corrected based on that distribution, but the effect on the scattered radiation by the positional misalignment due to deformation of the absorbing foil is not taken into account. Consequently, there is the danger that, conversely, false images will be produced through error in the scattered radiation intensity distribution due to the effect thereof 5. Moreover, in the method described above, proposed by the present applicant, the distance between the grid and the x-ray detector is set to an integer multiple of the height of the absorbing foil so that the sums of the viewing angles of the grid will be essentially identical from each pixel (where, in this method, an example is given wherein the distance between the grid and the x-ray detector is the same as the height of the absorbing foil). However, in practice there is an angular distribution in the grid viewing angles for the individual pixels, and the actual scattered radiation intensities will have intensity distributions in accordance with the viewing angle. Consequently, there is a high likelihood that there will be error in the scattered radiation intensity distribution calculated in the correction calculations.

6. Additionally, in the method described above, proposed by the present applicant, the grid position and shape of the absorbing foil are set so that the shadow of the absorbing foil will be contained within a constant pixel column or pixel row, even if there is a change in the position of the radiation emitting means, the grid, and the x-ray detector, but actually, often in, for example, a circulatory system imaging device, the distance between the radiation emitting means, the grid, and the x-ray detector are changed each time the imaging is performed. Consequently, use is only possible within a limited range in order to fulfill the conditions so that the shadow of the absorbing foil will be contained with in a constant pixel column or pixel row. Furthermore, it is necessary to be within the requirements for the deformation for the absorbing foil that structures the grid, and for the misalignment from the design position, and thus there are tight requirements for the mechanical precision and assembly precision, which are difficult to achieve from a cost perspective and technology perspective.

The present invention is the result of contemplation on this type of situation, and the object thereof is to provide a radiography device that can be applied also to general-use scattered radiation removal means, and capable of producing appropriate radiation images that are independently of the status of installation of the scattered radiation removing means.

SUMMARY OF THE INVENTION

The present invention, in order to achieve this object, is structured as follows:

The invention set forth is a radiography device for producing a radiation image, comprising: radiation emitting means for emitting radiation; scattered radiation removing means for removing scattered radiation; and radiation detecting means, wherein a plurality of detecting elements, for detecting radiation, is configured in an array; further comprising: pixel specifying means for specifying particular pixels from among the various pixels that structure the radiation image; intensity estimating means for estimating scattered radiation intensities at the particular pixels specified by the pixel specifying means and/or direct radiation intensities of the particular pixels; and intensity interpolating means for interpolating the scattered radiation intensities at pixels that were not specified and/or the direct radiation intensities at pixels that were not specified, based on the scattered radiation intensities and/or direct radiation intensities estimated by the intensity estimating means.

In the invention set forth in Claim 1, radiation is emitted from radiation emitting means, and is incident into the radiation detecting means through the scattered radiation removing means. A portion of the scattered radiation is removed by the scattered radiation removing means, and the radiation is detected by the radiation detecting means, to produce a radiation image. At this time, of the individual pixels that structure the radiation image, particular pixels are specified by the pixel specifying means. The scattered radiation intensities of the particular pixels specified by the pixel specifying means, and/or the direct radiation intensities of the particular pixels are estimated by the intensity estimating means. Consequently, it is possible to estimate appropriately the scattered radiation intensities and/or the direct radiation intensities at the particular pixels, taking into consideration the status of installation of the scattered radiation removing means. On the other hand, for those pixels that have not been specified, the following is performed. Based on the scattered radiation intensities and/or the direct radiation intensities estimated by the intensity estimating means, interpolation is performed by the intensity interpolating means for radiation intensities that are the scattered radiation intensities for pixels that have not been specified or the direct radiation intensities for the pixels that have not been specified. Consequently, for specified pixels, the radiation intensity is estimated by the intensity estimating means, and for pixels that have not been specified, the radiation intensity is interpolated by the intensity interpolating means. A radiation image can the be obtained appropriately based on such radiation intensities, and the shadows of the scattered radiation removing means are eliminated to produce a radiation image of only the direct radiation, from which the scattered radiation has been completely removed. In the radiation images that can be obtained by these pixel specifying means, the intensity estimating means, and the intensity interpolating means, can be obtained appropriately with any scattered radiation removing means, without depending on any particular scattered radiation removing means (for example, a synchronized grid). The result is the possibility of application also to general-use scattered radiation removing means, making it possible to obtain an appropriate radiation image, independently of the status of installation of the scattered radiation removing means. Additionally, it is not necessary to estimate the radiation intensities for all of the pixels, but rather only the radiation intensities for specified particular pixels need be estimated and the radiation intensities of the remaining pixels that were not specified may be calculated through performing interpolation, and thus there is the effect of being able to reduce and shorten the time required by the calculation processing.

One example of scattered radiation removing means used in the invention set forth above is as follows. The scattered radiation removing means are structured so that the layout direction of the absorbing layer for absorbing the scattered radiation is parallel to the row direction and/or the column direction of the detecting elements, and the spacing between adjacent absorbing layers is an integer multiple of the spacing between adjacent pixels. That is, the scattered radiation removing means structured in this way, are a synchronized grid. In the case of a synchronized grid, the offsets between the pixels and the absorbing layer and another layer (a middle layer) have periodicity matching the offsets between the individual pixels, and thus it is possible to perform the calculations regularly and periodically. Consequently, the processing becomes simple, enabling the calculation processes to be performed easily and quickly. The result is the ability to not only estimate the radiation intensity more easily, but also to interpolate the radiation intensity as well.

In the invention described above, preferably the transmissivity is calculated in advance by performing, in advance, radiography in a state wherein no test subject is present. That is, the radiation emitting means emit radiation in a state wherein no test subject is present, and that radiation is transmitted through the scattered radiation removing means to be incident on the radiation detecting means, to produce actual measurement data in a state wherein no test subject is present. Transmissivity calculating means are provided for calculating direct radiation transmissivity, which is the ratio of transmission before and after the transmission of the direct radiation through the scattered radiation removing means, calculated through the actual measurement in a state wherein no test subject is present. The provision of the transmissivity calculating means enables the calculation of the direct radiation transmissivity.

Preferably, when the distance between the radiation emitting means, the scattered radiation removing means, and the radiation detecting means is varied, transmissivity interpolating means are provided wherein the direct radiation transmissivity is calculated by the transmissivity calculating means at discrete distances between the radiation emitting means, the scattered radiation removing means, and the radiation detecting means, and, based on the direct radiation transmissivities calculated by the transmissivity calculating means, the direct radiation transmissivities are interpolated for distances before and after the discrete distances. The provision of the transmissivity calculating means and the transmissivity interpolating means in this way enables the calculation of the direct radiation transmissivity in response to the distance even when the distance between the radiation emitting means, the scattered radiation removing means, and the radiation detecting means is varied.

The direct radiation transmissivities are used to produce a radiation image in a state wherein an actual test subject is present (for example, a phantom). That is, the radiation emitting means emit radiation in a state wherein there is an actual test subject, and the radiation is passed through the scattered radiation removing means to be incident on the radiation detecting means, to produce actual measured intensities that are the radiation intensities after transmission through the scattered radiation removing means in an actual measurement in a state wherein a test subject is present, by having the radiation pass through the scattered radiation removing means to be incident onto the radiation detecting means. The intensity estimating means estimate the radiation intensities for particular pixels, specified by the pixel specifying means based on the direct radiation transmissivities calculated by the transmissivity calculating means or on the direct radiation transmissivities interpolated by the transmissivity interpolating means, and the actual measured intensities, described above, in the actual measurement in the state wherein a test subject is present. This enables the calculation of the direct radiation transmissivities based on actual measured data in a state wherein no test subject is present, enabling the estimation of the radiation intensities based on the actual measured intensities in a state wherein a test subject is present, using that direct radiation transmissivity.

Specifically, when estimating unknown radiation intensities at particular pixels specified by the pixel specifying means, the number of particular pixels to be specified by the pixel specifying means is determined in accordance with a number of knowns for known direct radiation transmissivities and a number of knowns for known actual measured intensities, and the intensity estimating means solves a system of simultaneous equations regarding the actual measured intensities for each particular pixel that has been specified, the direct radiation transmissivity thereof, and the radiation intensity thereof to estimate the radiation intensities. The radiation intensities can be estimated easily through solving the system of simultaneous equations.

Because there is the danger of not being able to solve accurately the system of simultaneous equations when the absolute value of the denominator included in the solution of the simultaneous equations is less than a specific value, preferably the following is performed. In such a case, the pixel specifying means selects and specifies another combination of particular pixels, rather than selecting the particular pixels that formed that system of simultaneous equations, where solving the system of simultaneous equations for each set of particular pixels that is specified in this way, where the intensity estimating means estimate the radiation intensities by solving the system of simultaneous equations for each set of the particular pixels that has been specified, and the interpolating means perform interpolation for the radiation intensities of the pixels that were not selected.

When solving the system of simultaneous equations, the estimations are performed as described below, as a more specific example. When the radiation intensities to be estimated are transmitted scattered radiation intensities that are the scattered radiation intensities after transmission through the scattered radiation removing means, and estimated direct radiation intensities that are the direct radiation intensities after transmission through the test subject and prior to transmission through the scattered radiation removing means, the number of particular pixels to be specified by the pixel specifying means in accordance with the number of knowns of known direct radiation transmissivities and the number of knowns of known actual measured values is determined to be 3. Given this, a combination of three pixels, comprising an (n−1)th pixel, the nth pixel that is adjacent thereto, and the (n+1)th pixel that is adjacent thereto is specified. For each of the three adjacent pixels (n−1), n, and (n+1), if the actual measured intensities are defined as $G_{n-1}$, $G_n$, and $G_{n+1}$, the direct radiation transmissivities are defined as $Cp_{n-1}$, $Cp_n$, and $Cp_{n+1}$, the transmitted scattered radiation intensities are defined as $Sc_{n-1}$, $Sc_n$, and $Sc_{n+1}$, and the estimated direct radiation intensities are defined as $P_{n-1}$, $P_n$, and $P_{n+1}$, then the intensity estimating means can estimate the transmitted scattered radiation intensity and/or the estimated direct radiation intensity by solving the system of equations obtained from Equation (A), Equation (B), Equation (B-2), Equation (B-3), and Equation (C).

Equation (A) is an equation for calculating the transmitted scattered radiation intensity for each pixel through interpolation calculations of the transmitted scattered radiation intensities of the adjacent pixels, and is expressed by:

$$Sc_n = (Sc_{n+1} + Sc_{n-1})/2 \tag{A}$$

Equations (B-1), (B-2), and (B-3) are a system of simultaneous equations for each set of three adjacent pixels (n−1), n, and (n+1), wherein the actual measured intensities are set equal to the sum of the product of the estimated direct radiation intensity and the direct radiation transmissivity plus the transmitted scattered radiation intensity, and are expressed by the following:

$$G_{n+1} = P_{n+1} \cdot Cp_{n+1} + Sc_{n+1} \tag{B-1}$$

$$Gn = Pn \cdot Cpn + Sc_n \tag{B-2}$$

$$G_{n-1} = P_{n-1} \cdot Cp_{n-1} + Sc_{n-1} \tag{B-3}$$

Additionally, Equation (C) is an equation wherein the estimated direct radiation intensity is set to be equal for the three adjacent pixels, and is expressed by the following:

$$P_{n-1} = Pn = P_{n+1} \tag{C}$$

The transmitted scattered radiation intensities and the estimated direct radiation intensities can be estimated easily through solving the system of simultaneous equations obtained from these Equation (A), Equations (B-1), (B-2), and (B-3), and Equation (C). Additionally, a system of equations of this type is useful when using, as a test subject, an acrylic plate phantom, for example, wherein the direct radiation transmission thicknesses are uniform, or in other words, wherein the estimated direct radiation intensities are considered to be identical values for every pixel. Note that in the present specification, a "pixel" includes, of course, a single pixel wherein no binning process has been applied, and also includes the case wherein a plurality of pixels have been binned together and treated as a single pixel.

Furthermore, in the case of solving the system of simultaneous equations, estimations may be performed as follows, as another, more detailed, example. As with the example described above, when the radiation intensities to be estimated are transmitted scattered radiation intensities that are the scattered radiation intensities after transmission through the scattered radiation removing means, and estimated direct radiation intensities that are the direct radiation intensities after transmission through the test subject and prior to transmission through the scattered radiation removing means, the number of particular pixels to be specified by the pixel specifying means in accordance with the number of knowns of known direct radiation transmissivities and the number of knowns of known actual measured values is determined to be 3. Given this, a combination of three pixels, comprising an (n−1)th pixel, the nth pixel that is adjacent thereto, and the (n+1)th pixel that is adjacent thereto is specified. For each of the three adjacent pixels (n−1), n, and (n+1), if the actual measured intensities are defined as $G_{n-1}$, $G_n$, and $G_{n+1}$, the direct radiation transmissivities are defined as $Cp_{n-1}$, $Cp_n$, and $Cp_{n+1}$, the transmitted scattered radiation intensities are defined as $Sc_{n-1}$, $Sc_n$, and $Sc_{n+1}$, and the estimated direct radiation intensities are defined as $P_{n-1}$, $Pr_n$ and $P_{n+1}$, the estimations of the transmitted scattered radiation intensity and/or the estimated direct radiation intensity by solving the system of equations is the same as in the example above, but the conditions described below are added. That is, the estimated direct radiation intensity is expressed as the product of an estimated direct radiation distribution and a converting factor thereof, where this converting factor is defined as $a_n$, and, for each of three adjacent pixels (n−1), n, and (n+1), the estimated direct radiation distribution is defined as P(n−1), P(n), and P(n+1). At this time the intensity calculating means can estimate the transmitted scattered radiation intensities and the estimated direct radiation intensities through solving the system of simultaneous equations obtained from Equation (A), and Equations (B-1)', (B-2)', and (B-3)', below. As with the example above, equation (A) is an equation for calculating the transmitted scattered radiation intensity for each pixel through interpolation calculations of the transmitted scattered radiation intensities of the adjacent pixels, and is expressed by:

$$Sc_n = (Sc_{n+1} + Sc_{n-1})/2 \quad (A).$$

Equations (B-1)', (B-2)', and (B-3)' are a system of simultaneous equations for each set of three adjacent pixels (n−1), n, and (n+1), wherein the actual measured intensities are set equal to the sum of the product of the estimated direct radiation intensity and the direct radiation transmissivity plus the transmitted scattered radiation intensity, and are expressed by the following:

$$G_{n+1} = a_n \cdot P(n+1) \cdot Cp_{n+1} + Sc_{n+1} \quad (B\text{-}1)'$$

$$Gn = a_n \cdot P(n) \cdot Cpn + Sc_n \quad (B\text{-}2)'$$

$$G_{n-1} = a_n \cdot P(n-1) \cdot Cp_{n-1} + Sc_{n-1} \quad (B\text{-}3)'.$$

The transmitted scattered radiation intensities and the estimated direct radiation intensities can be estimated easily through solving the system of simultaneous equations obtained from these Equation (A), and Equations (B-1)', (B-2)', and (B-3)'.

Additionally, this type of system of simultaneous equations is useful in a case wherein a phantom that is near to the actual test subject (for example, in the case where the object is to image the torso portion of a human body, a water cylinder having essentially the same transmissivity thereof) is used as the test subject. In the case of this phantom, the estimated direct radiation distribution P(n) for each pixel n can be calculated through simulation calculations, and the system of simultaneous equations can be solved using known estimated direct radiation distributions.

In the these inventions as described above, preferably radiographic imaging is performed in advance in a state wherein no test subject is present, to calculate, in advance, the direct radiation transmissivities, and then radiographic imaging is performed in a state wherein a test subject is present (for example, an acrylic plate phantom or a water cylinder phantom), to establish reference intensities for all pixels pertaining to the radiation intensities, and then an average value or a value for each pixel calculated through smoothing or interpolation calculations is calculated, and a deviation rate, relative to those values, is calculated for each pixel. Conversely, more preferably, reference intensities are established for each pixel pertaining to the transmitted scattered radiation intensities, estimated using actual measurements using a dummy scattered radiation source in a state wherein no test subject is present, and then an average value or a value for each pixel calculated through smoothing or interpolation calculations is calculated, and a deviation rate, relative to those values, is calculated for each pixel. That is, in the former case, the radiation emitting means emit radiation in a state wherein a test subject is present (in this case, a phantom), where the radiation is radiated through the scattered radiation removing means to be incident on the radiation detecting means, to produce radiation intensities that are estimated by the intensity estimating means based on actual measurements in a state wherein a test subject is present (the phantom). In the latter, performing an actual measurement using a dummy scattered radiation source in a state wherein no test subject is present enables an estimation of the transmitted scattered radiation intensities, which are the scattered radiation intensities after transmission through the scattered radiation removing means, to obtain the estimated transmitted scattered radiation intensities. Deviation ratio calculating means for calculating the ratios of deviation for the estimated radiation intensities or the transmitted scattered radiation intensity are provided, and the deviation ratios calculated by the deviation ratio calculating means are reflected into the radiography for another test subject (a test subject used in the actual radiography).

Preferably, when the distance between the radiation emitting means, the scattered radiation removing means, and the radiation detecting means is varied, deviation ratio interpolating means are provided wherein the deviation ratios are calculated by the deviation ratio calculating means at discrete distances between the radiation emitting means, the scattered radiation removing means, and the radiation detecting means, and the deviation ratios are interpolated for distances before and after the discrete distances. The provision of the deviation ratio calculating means and the deviation ratio interpolating means in this way enables the calculation of the deviation ratios in response to the distance even when the distance between the radiation emitting means, the scattered radiation removing means, and the radiation detecting means is varied.

The specific detail of that which is reflected in this way is as follows. The radiation emitting means emit radiation with another test subject (which here is the test subject that is used in the actual radiation image) in a particular state, where the radiation is transmitted through the scattered radiation removing means to be incident on the radiation detecting means, to obtain actual measured intensities that are the radiation intensities after transmission through the scattered radiation removing means, in an actual measurement in the given state for the test subject. The intensity estimating means estimate the radiation intensities for the particular pixels specified by the pixel specifying means based on the deviation ratios calculated by the deviation ratio calculating means or the deviation ratios interpolated by the deviation ratio interpolating means, on the direct radiation transmission ratios calculated by the transmission ratio calculating means or the direct radiation transmission ratios interpolated by the transmission ratio interpolating means, and on the actual measured intensities, described above, actually measured in the state wherein there is another test subject (the test subject that is used in the actual radiography). In this way, the radiation intensities can be estimated based on the actual measured intensities in a state wherein a test subject is present (the test subject used in the actual radiography) by calculating direct radiation transmissivities based on actual measurement data in a state wherein no test subject is present, calculating deviation ratios, using those direct radiation transmissivities, through performing radiography in a state wherein a test subject is present (which, at this point, is a phantom), and then using those deviation ratios, or deviation ratios interpolated by the deviation ratio interpolating means, when performing radiography in a state wherein there is another test subject (which, at this point, is the test subject that is used in the actual radiography).

Specifically, the intensity estimating means, when estimating radiation intensities that are unknown at the particular pixels specified by the pixel specifying means estimate the radiation intensities by determining the number of particular pixels to be specified by the pixel specifying means in accordance with the number of knowns for known deviation ratios, the number of knowns for known direct radiation transmissivities, and the number of knowns for known actual measured intensities, and then solving a system of simultaneous equations regarding the actual measured intensities, direct radiation transmissivities, and regarding the radiation intensities to be estimated, for each of the particular pixels thus determined. The radiation intensities can be estimated easily through solving the system of simultaneous equations.

Because there is the danger of not being able to solve accurately the system of simultaneous equations when the absolute value of the denominator included in the solution of the simultaneous equations is less than a specific value, preferably the following is performed. In such a case, the pixel specifying means selects and specifies another combination of particular pixels, rather than selecting the particular pixels that formed that system of simultaneous equations, where solving the system of simultaneous equations for each set of particular pixels that is specified in this way, where the intensity estimating means estimate the radiation intensities by solving the system of simultaneous equations for each set of the particular pixels that has been specified, and the interpolating means perform interpolation for the radiation intensities of the pixels that were not selected.

When solving the system of simultaneous equations, the estimations are performed as described below, as a more specific example. That is, when the deviation ratios are deviations ratios of the transmitted scattered radiation intensities after transmission through the scattered radiation removing means (where the deviations is due to nonuniformities in the foils in the scattered radiation removing means), and the radiation intensities to be estimated are transmitted scattered radiation intensities after scattering/transmission through another test subject and transmission through the scattered radiation removing means and estimated direct radiation intensities that are the direct radiation intensities after transmission through the test subject and prior to transmission through the scattered radiation removing means, the number of particular pixels to be specified by the pixel specifying means in accordance with the number of knowns of the known deviation ratios, the number of knowns of known direct radiation transmissivities, and the number of knowns of known actual measured values is determined to be 3. Given this, a combination of three pixels, comprising an (n−1)th pixel, the nth pixel that is adjacent thereto, and the (n+1)th pixel that is adjacent thereto is specified. For each of the three adjacent pixels (n−1), n, and (n+1), if the actual measured intensities are defined as $G_{n-1}$, $G_n$, and $G_{n+1}$, the deviation ratios are defined as $Rcs_{n-1}$, $Rcs_n$, and $Rcs_{n+1}$, the direct radiation transmissivities are defined as $Cp_{n-1}$, $Cp_n$, and $Cp_{n+1}$ (in the ideal state wherein the scattered radiation removing means have no nonuniformities in the foils, or the like), the transmitted scattered radiation intensities are defined as $Sc_{n-1}$, $Sc_n$, and $Sc_{n+1}$, and the estimated direct radiation intensities are defined as $P_{n-1}$, $P_n$, and $P_{n+1}$, then the intensity estimating means can estimate the transmitted scattered radiation intensity or the estimated direct radiation intensity by solving the system of equations obtained from Equation (A)", Equation (B)", Equation (B-2)", Equation (B-3), and Equation (C)". In Equation (A)" the transmitted scattered radiation intensities will be smooth and will not vary if the deviation ratios that result from the nonuniformities in the scattered radiation removing means are eliminated, and thus the transmitted scattered radiation intensities are identical across the three adjacent pixels, which is expressed as follows:

$$Sc_{n-1}=Sc_n=Sc_n+1 \quad (A)''.$$

Equations (B-1)", (B-2)", and (B-3)" are a system of simultaneous equations for each set of three adjacent pixels (n−1), n, and (n+1), wherein the actual measured intensities are set equal to the sum of the product of the estimated direct radiation intensity and the direct radiation transmissivity plus the transmitted scattered radiation intensity, and are expressed by the following:

$$G_{n+1}=P_{n+1} \cdot Cp_{n+1}+Sc_{n+1} \cdot Rcs_{n+1} \quad (B-1)''$$

$$Gn=Pn \cdot Cpn+Sc_n \cdot Rcs_n \quad (B-2)''$$

$$G_{n-1}=P_{n-1} \cdot Cp_{n-1}+Sc_{n-1} \cdot Rcs_{n-1} \quad (B-3)''.$$

Additionally, Equation (C) is an equation wherein the estimated direct radiation intensity is calculated through an interpolation calculation on the estimated direct radiation intensities of the adjacent pixels, and is expressed by the following:

$$P_n=(P_{n+1}+P_{n-1}) \quad (C)''$$

The transmitted scattered radiation intensities and the estimated direct radiation intensities can be estimated easily through solving the system of simultaneous equations obtained from these Equation (A)", Equations (B-1)", (B-2)", and (B-3)", and Equation (C)".

The invention is a radiography device for producing a radiation image, having: radiation emitting means for emitting radiation; scattered radiation removing means for removing scattered radiation; and radiation detecting means, wherein a plurality of detecting elements, for detecting radiation, is configured in an array; further including: estimated direct radiation intensity calculating means for calculating, through averaging or smoothing and interpolating, an estimated direct radiation intensity that is the direct radiation intensity after transmission through the test subject and prior to transmission through the scattered radiation removing means; and transmitted scattered radiation calculating means for calculating the transmitted scattered radiation intensity, which is the scattered radiation intensity after transmission through the scattered radiation removing means, based on the estimated direct radiation intensity calculated by the estimated direct radiation intensity calculating means.

Given the invention, if the test subject is of a known shape and material, such as a flat plate, a water cylinder, or the like, then if it is known that the estimated direct radiation intensities change smoothly, then the estimated direct radiation intensities can be calculated through averaging or through smoothing/interpolation. The averaging and the smoothing have the effect of reducing variability due to statistical fluctuation error, producing a value that is near to the true value for the estimated direct radiation intensities. The transmitted scattered radiation intensities are calculated based on the estimated direct radiation intensities that are near to the true values. Because the averaging or smoothing/interpolation calculations are not performed on the transmitted scattered radiation intensities, there is no decrease in the resolution of the image of the transmitted scattered radiation intensities. Furthermore, this makes it possible to maintain the resolution of the transmitted scattered radiation intensities and calculate precisely the fine variations in the transmitted scattered radiation intensities due to, for example, deformation of the grid foil in the scattered radiation removing means.

Furthermore, the invention is a radiography device for producing a radiation image, including: radiation emitting means for emitting radiation; scattered radiation removing means for removing scattered radiation; and radiation detecting means, wherein a plurality of detecting elements, for detecting radiation, is configured in an array; further having: transmitted scattered radiation calculating means for calculating through averaging or through smoothing/interpolation transmitted scattered radiation intensities, which are the scattered radiation intensities after transmission through the scattered radiation removing means; and direct radiation calculating means for calculating direct radiation intensities, which are the direct radiation intensities prior to transmission through the test subject and transmission through the scattered radiation removing means, based on the transmitted scattered radiation intensities calculated by the transmitted scattered radiation intensity calculating means.

Given the invention, if the radiation is x-ray radiation or γ-ray radiation, then it is known that if the test subject is a water cylinder or a human body, or the like, then the transmitted scattered radiation intensity will vary smoothly when compared to the estimated direct radiation intensity, so the transmitted scattered radiation intensity can be calculated through averaging or smoothing/interpolation. The averaging and the smoothing have the effect of reducing variability due to statistical fluctuation error, producing a value that is near to the true value for the transmitted scattered radiation intensities. The estimated direct radiation intensities are calculated based on the transmitted scattered radiation intensities that are near to the true values. Because none averaging or smoothing/interpolation calculations are performed on the estimated direct radiation intensities, there is no loss of resolution in the image of the estimated direct radiation intensities, enabling precise calculations of fine changes for fine changes in the shape and materials of the test subject.

The radiography device according to the present invention makes it possible to obtain an appropriate radiation image, independently of the status of installation of scattered radiation removing means, through enabling the application to even general-use scattered radiation removing means through: the pixel specifying means specifying particular pixels from among the pixels that structure a radiation image; the intensity estimating means estimating radiation intensities that are scattered radiation intensities of particular pixels that are specified by the pixel specifying means and/or direct radiation intensities of the specified pixels; and, based on the radiation intensities that are the scattered radiation intensities and/or the direct radiation intensities, estimated by the intensity estimating means, the intensity interpolating means interpolating radiation intensities that are the scattered radiation intensities of pixels that have not been specified and/or the direct radiation intensities of pixels that have not been specified.

DETAILED DESCRIPTION OF THE INVENTION

Figure 1:
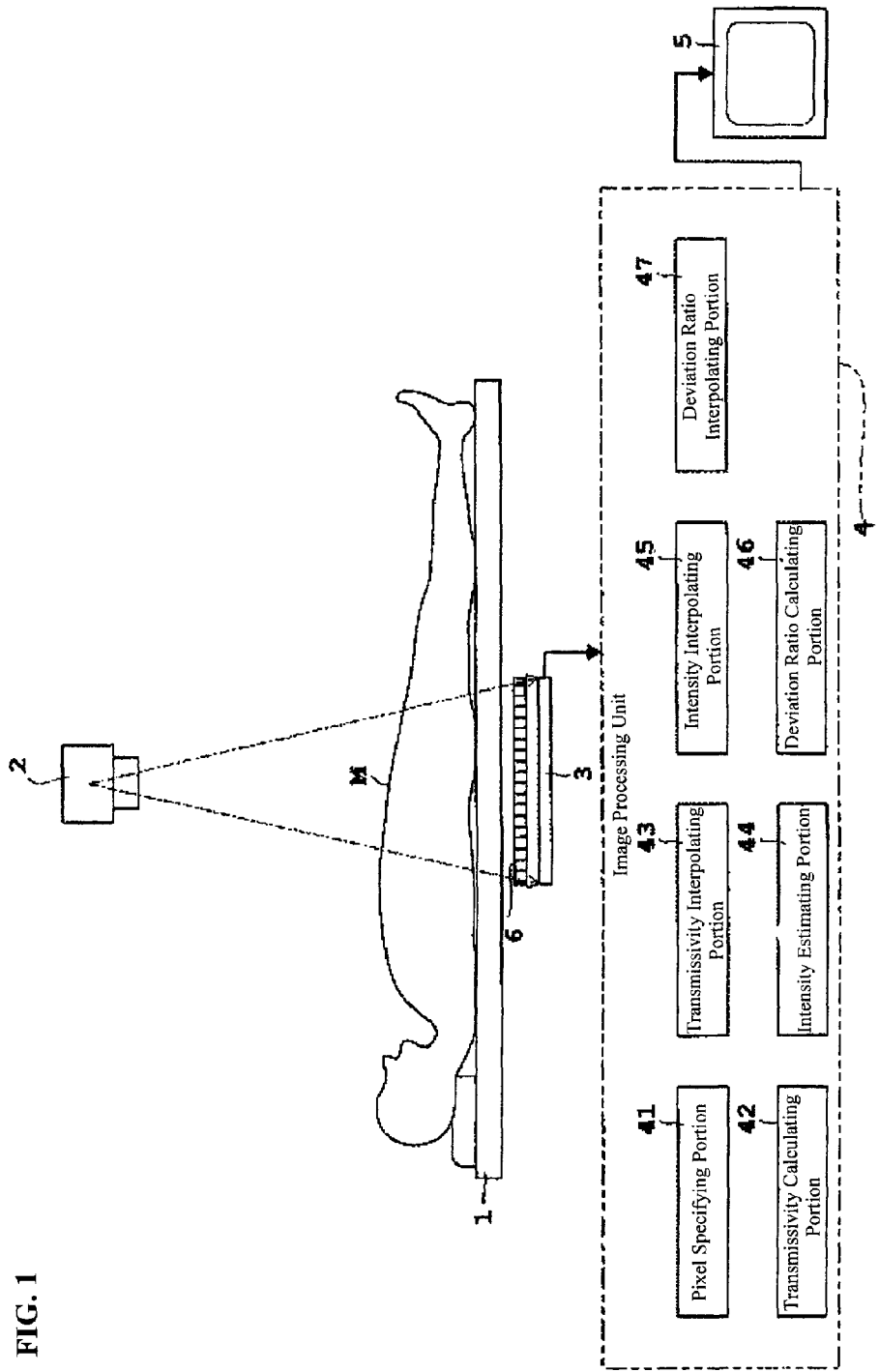
FIG. 1 is a block diagram of an x-ray radiography device according to the first and second examples of embodiment.
Figure 2:
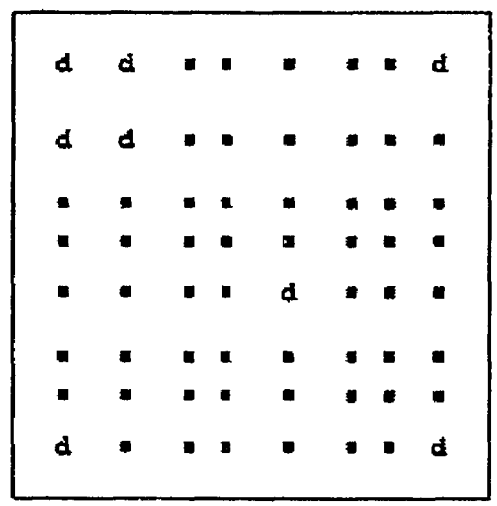
FIG. 2 is a schematic diagram of the detecting surface of a flat panel-type x-ray detecting device (FPD).
Figure 3:
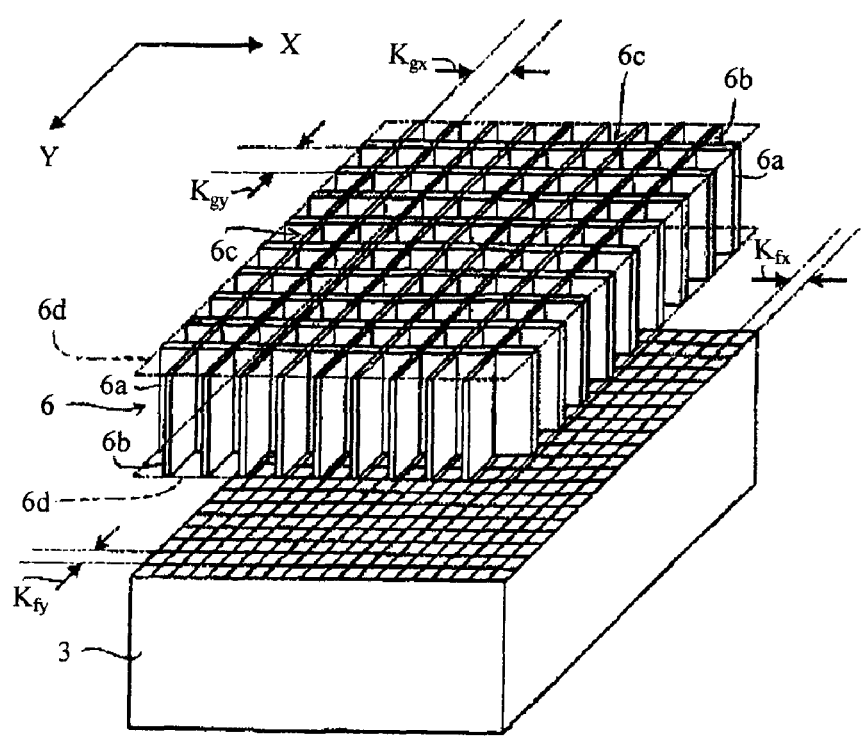
FIG. 3 is a schematic diagram of a synchronized cross grid.

A first example of embodiment according to the present invention will be explained below referencing the figures. FIG. 1 is a block diagram of an x-ray radiography device according to the first example of embodiment, including the second example of embodiment, described below; FIG. 2 is a schematic diagram of a detecting surface of a flat panel-type x-ray detector (FPD); and FIG. 3 is a schematic diagram of a synchronized cross grid. Moreover, in the first example of embodiment, which includes the second example of embodiment, described below, x-rays will be used in the explanation as an example of the radiation.

The x-ray radiography device as set forth in the first example of embodiment, which includes the second example of embodiment, described below, as illustrated in FIG. 1, includes: a ceiling plate 1 upon which is placed a test subject M; an x-ray tube for emitting an x-ray in the direction of the test subject M; a flat panel x-ray detector (hereinafter termed an "FPD") 3 for detecting x-rays that have been emitted from the x-ray tube 2 and transmitted through the test subject M; an image processing unit 4 for performing image processing based on the x-rays detected by the FPD 3; and a display unit 5 for displaying an x-ray image that has undergone various types of image processing by the image processing unit 4. The display unit 5 is structured from displaying means such as a monitor, a television, or the like. Furthermore, a grid 6 is disposed on the detecting surface side of the FPD 3. The x-ray tube 2 corresponds to the radiation emitting means in the present invention, the flat panel x-ray detector (FPD) 3 corresponds to the radiation detecting means in the present invention, and the grid 6 corresponds to the scattered radiation removing means in the present invention.

The image processing unit is structured from a central calculation processing device (CPU). Note that programs, and the like, for performing various types of image processing are written to and stored on a storage medium such as typified by a read-only memory (ROM), or the like, where the program, and the like, is read out from the storage medium and executed by the CPU of the image processing unit 4 to perform the image processing in accordance with the program. In particular, a pixel specifying portion 41, a transmissivity calculating portion 42, a transmissivity interpolating portion 43, an intensity estimating portion 44, an intensity interpolating portion 45, a deviation ratio calculating portion 46, and a deviation ratio interpolating portion 47, described below, of the image processing unit 4 perform, respectively, specification of particular pixels, estimation and interpolation of direct radiation transmissivities, estimation and interpolation of intensities, and calculation and interpolation of deviation ratios in accordance with the programs through the execution of programs pertaining to specifying particular pixels, calculating and interpolating direct radiation transmissivities, estimating and interpolating intensities, and calculating and interpolating deviation ratios.

The image processing unit 4 has: a pixel specifying portion 41 for specifying particular pixels; a transmissivity calculating portion 42 for calculating direct radiation transmissivities; a transmissivity interpolating portion 43 for interpolating direct radiation transmissivities; an intensity estimating portion 44 for estimating intensities; an intensity interpolating portion 45 for interpolating intensities; a deviation ratio calculating portion 46 for calculating deviation ratios; and a deviation ratio interpolating portion 47 for interpolating deviation ratios. The pixel specifying portion 41 corresponds to the pixel specifying means in the present invention; the transmissivity calculating portion 42 corresponds to the transmissivity calculating means in the present invention; the transmissivity interpolating portion 43 corresponds to the transmissivity interpolating means in the present invention; the intensity estimating portion 44 corresponds to the intensity estimating means in the present invention; the intensity interpolating portion 45 corresponds to the intensity interpolating means in the present invention; the deviation ratio calculating portion 46 corresponds to the deviation ratio calculating means in the present invention; and the deviation ratio interpolating portion 47 corresponds to the deviation ratio interpolating means in the present invention. Additionally, the intensity estimating portion 44 corresponds also to the estimated direct radiation intensity calculating means and the transmitted scattered radiation intensity calculating means in the present invention.

The FPD 3, as illustrated in FIG. 2, is structured through the arraying of a plurality of x-ray-sensitive detecting elements d in the shape of a two-dimensional matrix on a detecting surface. The detecting elements d detect x-rays through converting into an electric signal x-rays that have been transmitted through the test subject M, temporarily storing the electric signals, and reading out the electric signals that have been stored. The electric signals from the respective detections by each of the individual detecting elements d are converted into pixel values in accordance with the electric signals thereof, and the pixel values are assigned to the pixels corresponding to the respective positions of the detection elements d, to output an x-ray image, and the x-ray image is sent to the pixel specifying portion 41, the transmissivity calculating portion 42, and the intensity estimating portion 44 of the image processing unit 4 (shown in FIG. 1 and FIG. 4). In this way, in the FPD 3, a plurality of detecting elements d that detect x-rays is configured into the shape of a matrix (a two-dimensional matrix shape). The detecting elements d correspond to the detecting elements in the present invention.

The grid 6, as illustrated in FIG. 3 is configured through arranging alternatingly absorbing foils 6a and 6b that absorb scattered radiation (scattered x-rays) and a middle layer 6c through which the scattered radiation passes. A grid cover 6d that covers the absorbing foils 6a and 6b and the middle layer 6c, has the absorbing foils 6a and 6b and the middle layer 6c held between the x-ray incident surface and the surface on the opposite side. In order to clarify the drawing of the absorbing foils 6a and 6b, the grid cover 6d is illustrated by the double dotted line, and the other structures in the grid 6 (the mechanisms for supporting the absorbing foils 6a and 6b, and the like) are omitted from the drawing. The absorbing foils 6a and 6b correspond to the absorbing layer in the present invention.

In the first example of embodiment, which includes the second example of embodiment, described below, a synchronized cross grid is used for the grid 6. Specifically, along with the absorbing foils 6a and the middle layers 6c that extend in the X direction in FIG. 3 and that are arranged alternatingly in the Y direction in FIG. 3, the absorbing foils 6b and the middle layer 6c that extend in the Y direction in FIG. 3 are arranged alternatingly in the X direction in FIG. 3, so that the absorbing foils 6a and the absorbing foils 6b cross each other. Here the X direction in FIG. 3 is parallel to the row direction of the detecting elements d in the FPD 3 (illustrated in FIG. 2), and the Y direction in FIG. 3 is parallel to the column direction of the detecting elements d in the FPD 3 (illustrated in FIG. 2). Consequently, in the first example of embodiment, the layout direction of the absorbing foils 6a and 6b are parallel to both directions, the row direction and the column direction, of the detecting elements d.

Additionally, in the Y direction, the spacing $K_{gy}$ between the mutually adjacent absorbing foils 6a is synchronized through being an integer multiple of the spacing $K_{fy}$ between the mutually adjacent pixels (illustrated in FIG. 3 as being twice the spacing). Similarly, in the X direction, the spacing $K_{gx}$ between mutually adjacent absorbing foils 6b is synchronized by being an integer multiple of the spacing $K_{fx}$ between mutually adjacent pixels (illustrated in FIG. 3 as being twice the spacing). In this way, the synchronized cross grid is structured so that the layout directions of the absorbing foils 6a and 6b are parallel to both the row direction and the column direction of the detecting elements d, and the spacings $K_{gy}$ and $K_{gx}$ between mutually adjacent absorbing foils 6a and 6b are multiple integers of the spacings $K_{fy}$ and $K_{fx}$ between mutually adjacent pixels.

In the first example of embodiment, which includes the second example of embodiment, described below, the middle layer 6c is an air gap. Consequently, the grid 6 is also an air grid. Note that for the absorbing foils 6a and 6b, insofar as the material is a material that absorbs radiation, as represented by x-rays, such as lead, or the like, there are no particular limitations on the material. For the middle layer 6c, there are no particular limitations insofar as the middle material is one through which the radiation, which is represented by the x-rays, can pass, such as aluminum or an organic substance, instead of an air gap.

Figure 4:
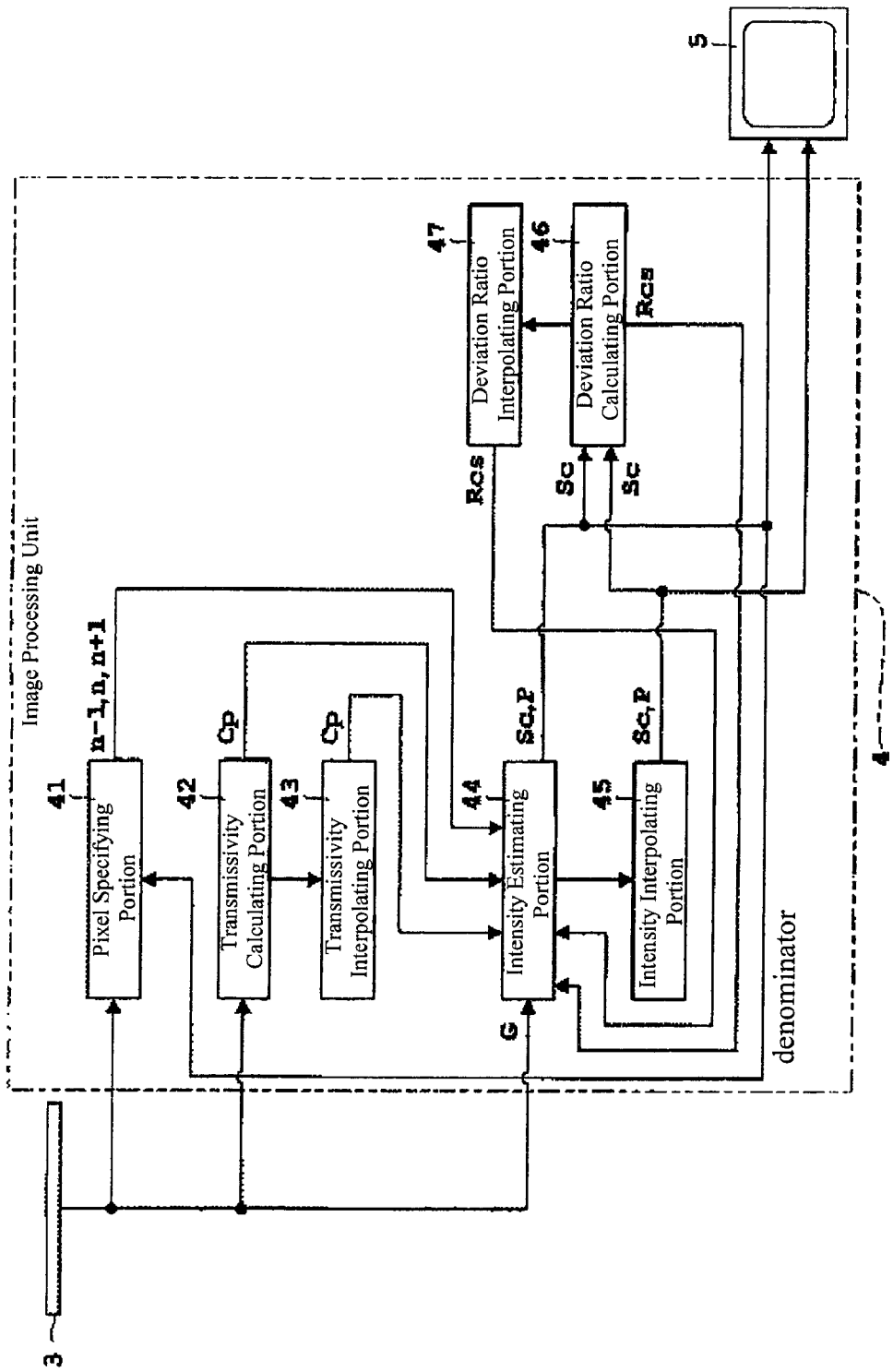
FIG. 4 is a block diagram illustrating the structure and the flow of data in a specific image processing unit in the first and second examples of embodiment.
Figure 5:
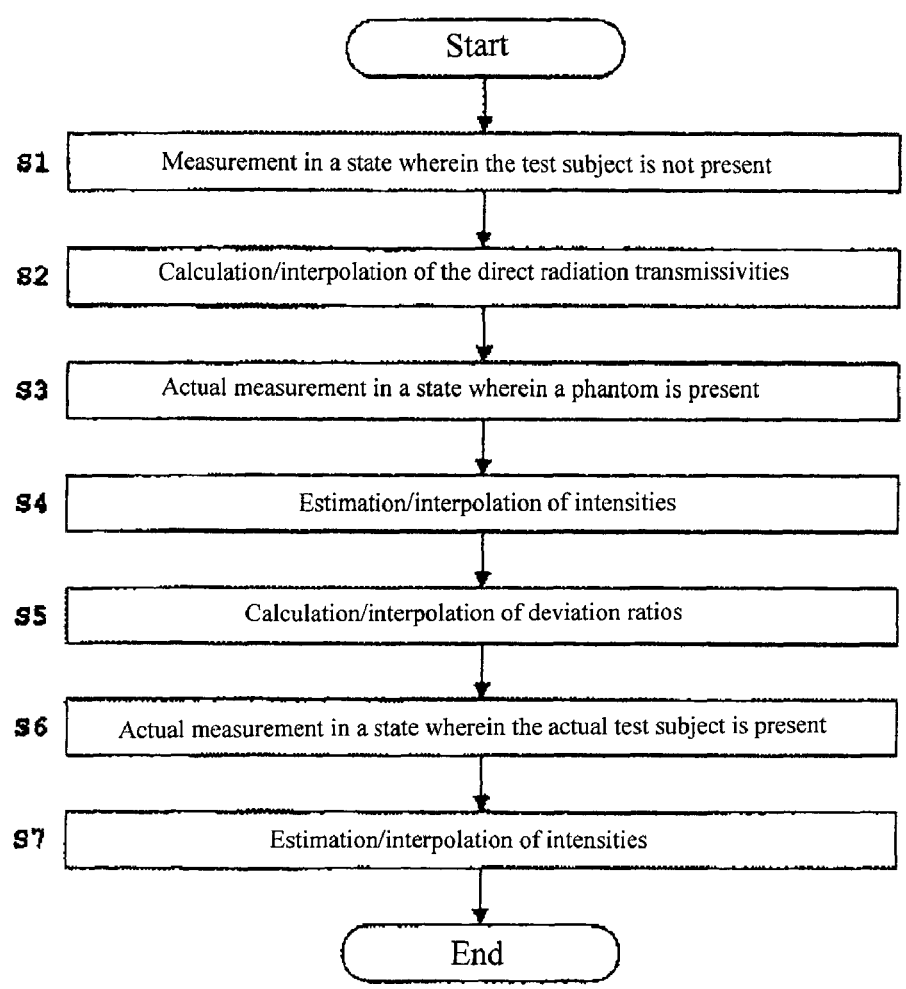
FIG. 5 is a flowchart illustrating the flow in the series of x-ray radiography as set forth in the first and second examples of embodiment.
Figure 6:
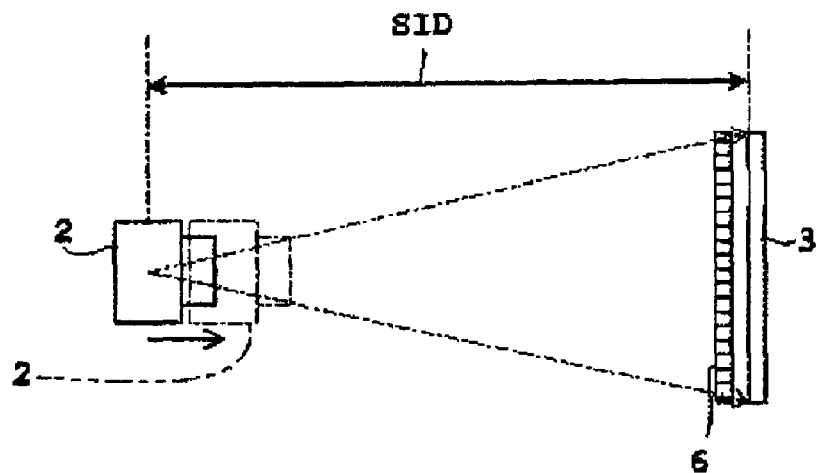
FIG. 6 is a diagram illustrating schematically x-ray radiography in the state wherein the test subject not present.
Figure 7:
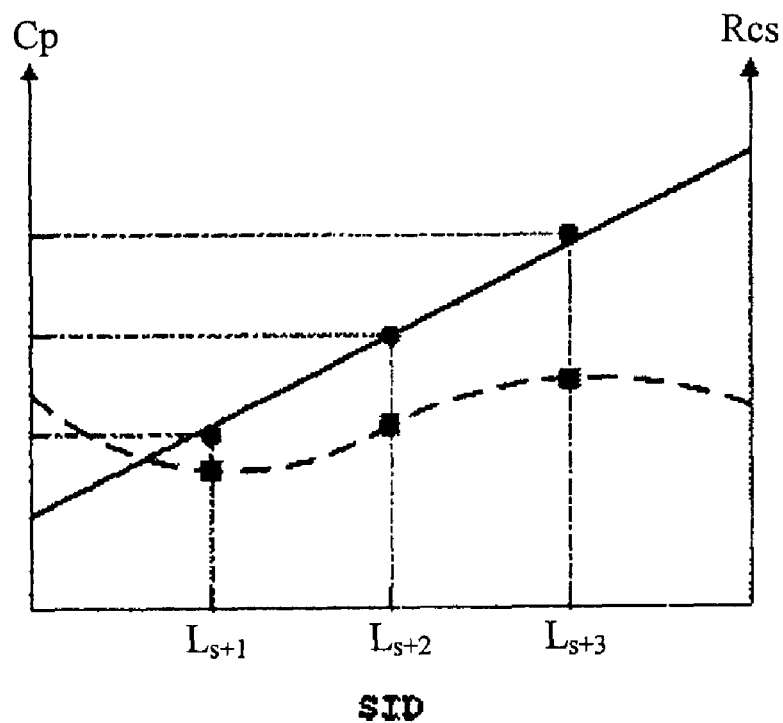
FIG. 7 is a graph illustrating schematically the relationship between the SID, the direct radiation transmissivity, and the deviation ratio.
Figure 8:
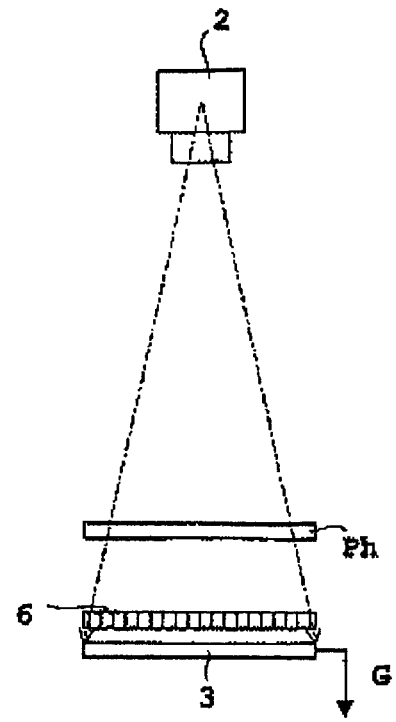
FIG. 8 is a diagram illustrating schematically x-ray radiography in a state wherein a test subject is present according to a first form of embodiment in the case wherein an acrylic plate phantom is used as the test subject.

The actual x-ray radiography and flow of data in the first example of embodiment, which includes the second example of embodiment, described below, will be described in reference to FIG. 4 through FIG. 8. FIG. 4 is a block diagram illustrating a specific configuration for the image processing unit, and the flow of data therein; FIG. 5 is a flowchart illustrating the flow in the series of x-ray radiography; FIG. 6 is a diagram illustrating schematically x-ray radiography in a state wherein the test subject not present; FIG. 7 is a graph illustrating schematically the relationship between the SIDs, the direct radiation transmissivities, and the deviation ratios; and FIG. 8 is a diagram illustrating schematically x-ray radiography in a state wherein a test subject is present, in accordance with the first example of embodiment, when an acrylic plate phantom is used as the test subject.

As illustrated in FIG. 4, the pixel specifying portion 41 specifies particular pixels from among all of the pixels that structure the x-ray image. In the first example of embodiment, which includes the second example of embodiment, described below, the pixel specifying portion 41 specifies a combination of three pixels, comprising the (n−1)th pixel, the nth pixel adjacent thereto, and the (n+1)th pixel adjacent thereto (indicated as "n−1", "n", and "n+1" in FIG. 4), and sends these to the intensity estimating portion 44. Note that if the absolute value of the denominator included in the solution of the system of simultaneous equations, described above, is equal to or less than a specific value (if the denominator is "0" in the first example of embodiment, which includes the second example of embodiment, described below), then the pixel specifying portion 41 selects and specifies another combination of particular pixels, instead of selecting particular pixels to produce that combination of simultaneous equations. As is clear from the explanation below, the system of simultaneous equations is calculated by the intensity estimating portion 44, and thus data pertaining to the denominator, calculated by the intensity estimating portion 44 (indicated by the word "denominator" in FIG. 4) is sent to the pixel specifying portion 41.

The direct radiation transmissivity, which is the ratio of transmission from prior to transmission and after transmission of the direct radiation (the direct x-rays) through the grid 6, calculated through actual measurement in a state wherein the test subject not present, is calculated by the transmissivity calculating portion 42 for discrete distances between the x-ray tube 2, the grid 6, and the FPD 3. In the first example of embodiment, which includes the second example of embodiment, described below, the transmissivity calculating portion 42 calculates the direct radiation transmissivity (indicated by "Cp" in FIG. 4), and sends the direct radiation transmissivity to the transmissivity interpolating portion 43 and the intensity estimating portion 44.

The transmissivity interpolating portion 43 performs interpolation of the direct radiation transmissivities Cp, calculated by the transmissivity calculating portion 42, for before and after the aforementioned discrete distances. Then the interpolated direct radiation transmissivities Cp are also sent to the intensity estimating portion 44.

The intensity estimating portion 44 estimates the scattered radiation intensities (scattered x-ray intensities) of the particular pixels specified by the pixel specifying portion 41 and/or the direct radiation intensities (direct x-ray intensities) at the particular pixels. In the first example of embodiment, which includes the second example of embodiment, described below, the intensity estimating portion 44 estimates the transmitted scattered radiation intensities (indicated by "Sc" in FIG. 4) and the estimated direct radiation intensities (indicated by "P" in FIG. 4) based on the direct radiation transmissivities Cp, calculated by the transmissivity calculating portion 42, or the direct radiation transmissivities Cp, interpolated by the transmissivity interpolating portion 43, and the actual measured intensities (indicated by "G" in FIG. 4), which are the intensities after having been transmitted through the grid 6, of an actual measurement in a state wherein a test subject M is present, and sends the results to the intensity interpolating portion 45, the deviation ratio calculating portion 46, the display unit 5, and/or the like. Additionally, in the first example of embodiment, which includes the second example of embodiment, described below, the transmitted scattered radiation intensities Sc and/or the estimated direct radiation intensities P are estimated through the intensity estimating portion 44 solving a system of simultaneous equations, and thus there will be data "denominator" regarding the denominator included in the solution to the system of simultaneous equations, and this data "denominator" pertaining to the denominator is sent to the pixel specifying portion 41.

The intensity interpolating portion 45 performs interpolation between the scattered radiation intensity (scattered x-ray intensity) at the particular pixels estimated by the intensity estimating portion 44 and/or between the direct radiation intensity (direct x-ray intensity) at the particular pixels. In the first example of embodiment, which includes the second example of embodiment, described below, the intensity interpolating portion 45 performs interpolation between the transmitted scattered radiation intensities Sc or the estimated direct radiation intensities P, estimated by the intensity estimating portion 44, and sends the results to the deviation ratio calculating portion 46, the display unit 5, and/or the like.

The deviation ratio calculating portion 46 uses the intensities estimated by the intensity estimating portion 44 based on the actual measurements in a state wherein a test subject M is present to calculate an average value or a value for each individual pixel, calculated through a smoothing/interpolation calculation, as a reference intensity regarding the intensity for each individual pixel, and calculates a deviation ratio for each individual pixel based on this value/these values. Then the deviation ratios estimated by the deviation ratio calculating portion 46 or deviation ratios interpolated by a deviation ratio interpolating portion 47 are used and applied to the x-ray radiography for another test subject M. In the first example of embodiment, which includes the second example of embodiment, described below, the transmitted scattered radiation intensities Sc, estimated by the intensity estimating portion 44, and the transmitted scattered radiation intensities Sc, interpolated by the intensity interpolating portion 45, are used to calculate the deviation ratios (indicated by "Rcs" in FIG. 4), and the results are sent again to the intensity estimating portion 44.

In the first example of embodiment, which includes the second example of embodiment, described below, the actual x-ray radiography has the flow illustrated in FIG. 5.

[Step S1] Actual Measurement in a State Wherein the Test Subject is Absent

X-ray imaging is performed in a state wherein the test subject for actual measurement not present. As is illustrated in FIG. 6, the x-rays from the x-ray tube 2 are emitted towards the grid 6 and the FPD 3, with no test subject interposed between the x-ray tube 2 and the grid 6, to form an x-ray image in a state wherein the test subject not present, to perform an actual measurement in a state wherein the test subject not present. That is, the x-ray tube 2 emits x-rays in a state wherein the test subject not present, and causes the x-rays to be incident on the FPD 3 through the grid 6, to produce actual measurement data in a state wherein the test subject not present. Specifically, in a state wherein the test subject not present, the detecting elements d of the FPD 3 (illustrated in FIG. 3) convert the x-rays into electric signals to read out the x-rays, to convert into pixel values in accordance with the electric signals.

[Step S2] Calculation/Interpolation of the Direct Radiation Transmissivities

The pixel values are equivalent to the intensities after transmission through the grid 6, obtained through actual measurements in a state wherein the test subject not present. On the other hand, because the intensities prior to transmission through the grid 6 are already known, the direct radiation transmissivities Cp, which are the ratios of intensities before transmission through the grid 6 (before transmission) and after transmission through the grid 6 (after transmission), are indicated by the ratios of the intensities prior to transmission through the grid 6 and the intensities after transmission through the grid 6 (that is, the pixel values detected by the FPD 3).

Given this, sending to the transmissivity calculating portion 42 the intensities after transmission through the grid 6, which are equivalent to the pixel values from the FPD 3, and the intensities prior to transmission through the grid 6, which are known in advance, enables the transmissivity calculating portion 42 to calculate the direct radiation transmissivities Cp that indicate the ratios of the intensities prior to transmission through the grid 6 and the intensities after transmission therethrough. The transmissivity calculating portion 42 calculates these direct radiation transmissivities Cp for discrete distances between the x-ray tube 2, the grid 6, and the FPD 3. The distances between the x-ray tube 2, the grid 6, and the FPD 3 are the distance from the focal point of the x-ray tube 2 to the detecting surface (the incidence surface) of the FPD 3 (the source-image distance (SID)), because the grid 6 and the FPD 3 are disposed in proximity to each other.

The distance SID from the focal point of the x-ray tube 2 varies, as illustrated in FIG. 6, in actual x-ray radiography. Given this, x-ray radiography is performed, similarly, in a state wherein the test subject not present, and, as indicated by the black circles in FIG. 7, the direct radiation transmissivities Cp are calculated by the transmissivity calculating portion 42 for each discrete distance $L_{s+1}$, $L_{s+2}$, $L_{s+3}$, and the like. The direct radiation transmissivities Cp for the discrete distances $L_{s+1}, L_{s+2}, L_{s+3}, \ldots$ are sent to the transmissivity interpolating portion 43, the intensity estimating portion 44, and the like. Note that the transmissivity calculating portion 42 calculates the direct radiation transmissivities Cp for each individual pixel as well, and sends the results to the transmissivity interpolating portion 43, the intensity estimating portion 44, and the like.

The transmissivity interpolating portion 43 interpolates the direct radiation transmissivities Cp, calculated by the transmissivity calculating portion 42, for distances before and after the discrete distances $L_{s+1}, L_{s+2}, L_{s+3}, \ldots$. The results of the interpolation are, for example, as illustrated by the solid line in FIG. 7. For the method for the interpolation, values obtained through the arithmetic mean (additive mean) or the geometric mean for two direct radiation transmissivities Cp for mutually adjacent discrete distances (for example, $L_{s+1}$ and $L_{s+2}$) may be calculated as the direct radiation transmissivity Cp for a distance between the aforementioned adjacent discrete distances, Legrange interpolation may be performed, a value corresponding to a distance on a line produced through the linear approximation in FIG. 7 using the least-squares method may be calculated as the direct radiation transmissivities Cp, and so forth, and there is no particular limitation insofar as the method is a commonly used interpolation method. The direct radiation transmissivities Cp interpolated by the transmissivity calculating portion 42 are sent to the intensity estimating portion 44.

[Step S3] Actual Measurement in a State Wherein a Phantom is Present

Figure 9:
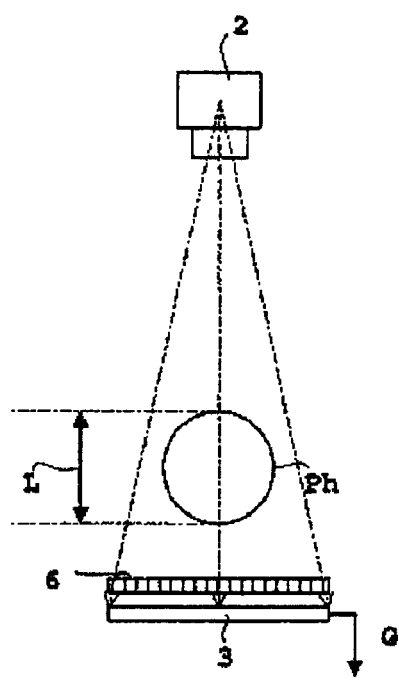
FIG. 9 is a diagram illustrating schematically x-ray radiography in the state wherein a test subject is present, according to a second example of embodiment in the case wherein a water cylinder phantom is used as the test subject.

X-ray imaging is next performed in a state wherein a test subject M is present. As illustrated in FIG. 8, an acrylic plate phantom Ph wherein the thickness for the transmission of the direct radiation is uniform, that is, wherein the estimated direct radiation intensities P are identical for all pixels, is used as the test subject M. Note that in the first example of embodiment, the phantom Ph, as illustrated in FIG. 8, is an acrylic plate, where, in the second example of embodiment, described below, the phantom Ph is a water cylinder, as illustrated in FIG. 9.

Returning to the explanation in the first example of embodiment, the acrylic plate phantom Ph is interposed between the x-ray tube 2 and the grid 6, and x-rays are emitted from the x-ray tube 2 in the direction of the grid 6 and the FPD 3, to perform actual measurements in a state wherein the phantom Ph is present, by performing x-ray radiography in the state wherein the phantom Ph is present. That is, the x-ray tube 2 emits x-rays in the state wherein the phantom Ph is present, and causes these x-rays to be transmitted through the grid 6 to be incident on the FPD 3, to produce actual measured intensities G, which are the intensities after transmission through the grid 6, in an actual measurement in the state wherein the phantom Ph is present. Specifically, the detecting elements d of the FPD 3 (illustrated in FIG. 3) convert the x-rays into electric signals to read out the x-rays in the state wherein the phantom Ph is present, to convert into pixel values in accordance with the electric signals.

[Step S4] Estimation/Interpolation of the Intensities

The pixel values are equivalent to the actual measured intensities G, which are the intensities after transmission through the grid 6 in an actual measurement in the state wherein the phantom Ph is present. On the other hand, the pixel specifying portion 41 specifies, as combinations of three pixels, three adjacent pixels (n−1), n, and (n+1), as described above. The intensity estimating portion 44 then estimates the transmitted scattered radiation intensities Sc and the estimated direct radiation intensities P at the three adjacent pixels (n−1), n, and (n+1), specified by the pixel specifying portion 41, based on the direct radiation transmissivities Cp calculated by the transmissivity calculating portion 42, the direct radiation transmissivities Cp interpolated by the transmissivity interpolating portion 43, and the actual measured intensities G, which are equivalent to the pixel values from the FPD 3.

Here the actual measured intensities G, are already known, calculated in the actual measurement in Step S3. The direct radiation transmissivities Cp were obtained through the actual measurement in Step S1, and were subjected to calculations/interpolations in Step S2, so are already known. On the other hand, the transmitted scattered radiation intensities Sc and the estimated direct radiation intensities P are values that are to be estimated by the intensity estimating portion 44, and are yet unknown at this point. Given this, the intensity estimating portion 44 estimates the transmitted scattered radiation intensities Sc and the estimated direct radiation intensities P by solving a system of simultaneous equations for each set of three adjacent pixels (n−1), n, and (n+1).

For each set of three adjacent pixels (n−1), n, and (n+1), the actual measured intensities G are defined as $G_{n-1}$, $G_n$, and $G_{n+1}$, the direct radiation transmissivities Cp are defined as $Cp_{n-1}$, $Cp_n$, and $Cp_{n+1}$, the transmitted scattered radiation intensities Sc are defined as $Sc_{n-1}$, $Sc_n$, and $Sc_{n+1}$, and the estimated direct radiation intensities P are defined as $P_{n-1}$, $P_n$, and $P_{n+1}$. The transmitted scattered radiation intensities Sc for the individual pixels will vary across the three adjacent pixels due to nonuniformities, and the like, in the grid 6 (the scattered radiation removing means), but this can be taken into account through calculating through the interpolation calculations of the transmitted scattered radiation intensities Sc of the adjacent pixels. In the first example of embodiment, the deviations in the transmitted scattered radiation intensity Sc within the three adjacent pixels (n−1), n, and (n+1) can be approximated through a linear approximation as in Equation (1), below:

$$Sc_n = (Sc_{n+1} + Sc_{n-1})/2 \quad (1)$$

The aforementioned Equation (1) corresponds to Equation (A) in the present invention.

Additionally, as was discussed regarding the interpolation for the direct radiation transmissivity Cp, Legrange interpolation, for example, may be used for the interpolation method for the transmitted scattered radiation intensity Sc, and there is no particular limitation to the aforementioned Equation (1) insofar as the interpolation is one that is commonly used.

The actual measured intensities G are expressed by the system of simultaneous equations (2) through (4), for each of the three adjacent pixels (n−1), n, and (n+1), wherein the actual measured intensity G is defined as equal to the sum of the transmitted scattered radiation intensity Sc added to the product of the estimated direct radiation intensity P· direct radiation transmissivity Cp:

$$G_{n+1} = P_{n+1} \cdot Cp_{n+1} + Sc_{n+1} \quad (2)$$

$$G_n = P_n \cdot Cp_n + Sc_n \quad (3)$$

$$G_{n-1} = P_{n-1} \cdot Cp_{n-1} + Sc_{n-1} \quad (4)$$

Equation (2) corresponds to Equation (B-1) in the present invention, Equation (3) corresponds to Equation (B-2) in the present invention, and Equation (4) corresponds to Equation (B-3) in the present invention.

As described above, because the acrylic plate that is used as the phantom Ph is formed so as to have a constant transmission thickness for the direct radiation, the estimated direct radiation intensity P can be expressed as in Equation (5), where the estimated direct radiation intensity P is set so as to be equal for all three of the pixels:

$$P_{n-1} = P_n = P_{n+1} \quad (5)$$

This Equation (5) corresponds to Equation (C) in the present invention.

In this way, when estimating the transmitted scattered radiation intensities Sc and the estimated direct radiation intensities P that are unknown at the three adjacent pixels (n−1), n, and (n+1), specified by the pixel specifying portion 41, the pixel specifying portion 41 determines a specific number of pixels to be specified, based on the number of knowns of known direct radiation transmissivities Cp and the number of knowns of known actual measured intensities G. Then the system of simultaneous equations pertaining to the actual measured intensity G, and the direct radiation transmissivity Cp for each particular pixel that has been determined, and the transmitted scattered radiation intensities Sc and estimated direct radiation intensities P to be estimated is solved by the intensity estimating portion 44, to estimate the transmitted scattered radiation intensities Sc and the estimated direct radiation intensities P.

In the aforementioned Equation (1), the transmitted scattered radiation intensity Sc for each individual pixel is an equation that is calculated through an interpolation calculation for the transmitted scattered radiation intensities Sc for the adjacent pixels, and thus the number of unknowns can be decreased by one. On the other hand, the aforementioned Equation (5) is an equation wherein the estimated direct radiation intensity P is equal across the three adjacent pixels, and thus the number of unknowns can be defined as 1. Consequently, in the rest of the system of simultaneous equations, except for Equation (1) and Equation (5), there may be a number of simultaneous equations established equal to the number of specified pixels, in which case the system of simultaneous equations is solvable if the pixel specifying portion 41 specifies a given number of pixels. In the first example of embodiment, this number is defined as 3, setting up simultaneous Equations (2) through (4).

The estimated direct radiation intensities $P_n$ ($=P_{n+1}=P_{n-1}$) and the transmitted scattered radiation intensities $Sc_{n-1}$, $Sc_n$, and $Sc_{n+1}$ can be calculated as given in Equation (6) through (9), below, by solving the system of simultaneous equations obtained through the aforementioned Equations (1) through (5):

$$Pn = (G_{n+1} + G_{n-1} - 2Gn)/(Cp_{n+1} + Cp_{n-1} - 2Cpn) \quad (6)$$

$$Sc_{n+1} = G_{n+1} - P_{n+1} \cdot Cp_{n+1} \quad (7)$$

$$Sc_n = G_n - P_n \cdot Cp_n \quad (8)$$

$$Sc_{n-1} = G_{n-1} - P_{n-1} \cdot Cp_{n-1} \quad (9)$$

In the aforementioned Equations (6) through (9), first the estimated direct radiation intensity P is calculated using the actual measured intensities $G_{n-1}$, $G_n$, and $G_{n+1}$, which are already known through Equation (6), described above, and the known direct radiation transmissivities $Cp_{n-1}$, $Cp_n$, and $Cp_{n+1}$, and after the estimated direct radiation intensity P is known, then the transmitted scattered radiation intensities $Sc_{n-1}$, $Sc_n$, and $Sc_{n+1}$ can each be calculated using the aforementioned Equations (7) through (9), using the now-known estimated direct radiation intensity $P_n$ ($=P_{n+1}=P_{n-1}$).

In this way, if the combination of three adjacent pixels (n−1), n, and (n+1) is defined as one set, then a single estimated direct radiation intensity $P_n$ can be calculated for each set; however, as discussed for Equation (5), above, the estimated direct radiation intensities $P_n$ must actually have identical values for the entire set in the combination of the three pixels. However, in practice, there will be differences due to the influence of the deviation in transmissivity for the scattered radiation at the peripheral portions of the grid 6, and there will be error due to statistical fluctuation error. The average value for the estimated direct radiation intensity $P_n$ in the center portion wherein there is little experimental error is calculated in order to reduce the error due to the status of insulation of the grid 6 and due to statistical fluctuation. For example, when the peripheral portions of the grid 6 are slightly different from each other, as described above, the aforementioned Equation (6) is used to calculate the estimated direct radiation intensities $P_n$ for each of multiple sets for combinations of three pixels (n−1), n, and (n+1) in the center portion of the grid 6, to calculate an average value P^. This average value P^ is again substituted into each of the Equations (2) through (4) (in other words, substituted into the Equations (10) through (12), which are a reformulation of the aforementioned Equations (7) through (9)), to again calculate each of the transmitted scattered radiation intensities $Sc_{n-1}$, $Sc_n$, and $Sc_{n+1}$, for each individual set.

$$Sc_{n+1} = G_{n+1} - P^{\wedge} \cdot Cp_{n+1} \quad (10)$$

$$Sc_n = G_n - P^{\wedge} \cdot Cp_n \quad (11)$$

$$Sc_{n-1} = G_{n-1} - P^{\wedge} \cdot Cp_{n-1} \quad (12)$$

In this way, the intensity estimating portion 44 calculates the respective transmitted scattered radiation intensities $Sc_{n-1}$, $Sc_n$, and $Sc_{n+1}$ using Equations (10) through (12), above. The transmitted scattered radiation intensities $Sc_{n-1}$, $Sc_n$, and $Sc_{n+1}$, estimated by the intensity estimating portion 44, are sent to the intensity interpolating portion 45, the deviation ratio calculating portion 46, the display unit 5, and the like.

Focusing here on the denominator that is included in the solution for the simultaneous equations of the aforementioned Equations (1) through (5), in the first example of embodiment, it is clear from Equation (6), above, that the denominator is "$Cp_{n+1}+Cp_{n-1}-2Cp_n$." Even when this Equation (6) is substituted into the Equations (7) through (9), above, the denominator will still be "$Cp_{n+1}+Cp_{n-1}-2Cp_n$." If the absolute value of this denominator "$Cp_{n+1}+Cp_{n-1}-2Cp_n$" is equal to or greater than a particular value, then there is the danger that it will not be possible to solve the system of simultaneous equations.

In particular, if the denominator "$Cp_{n+1}+Cp_{n-1}-2Cp_n$" is zero, then it will not be possible to solve the system of simultaneous equations of Equations (1) through (5). If the denominator "$Cp_{n+1}+Cp_{n-1}-2Cp_n$" is zero, that is, if the direct radiation transmissivities $Cp_n$ in the center pixel of these pixels is the arithmetic mean of the direct radiation transmissivities $Cp_{n+1}$ and $Cp_{n-1}$ of the adjacent pixels (that is, $Cp_{n+1}+Cp_{n-1}-2Cp_n=0$, or in other words, $Cp_n=(Cp_{n+1}+Cp_{n-1})/2$), then if the pixel specifying portion 41 were to select three pixels (n−1), n, and (n+1) that would produce this combination of simultaneous equations, then the system of simultaneous equations could not be solved. Preferably, when the denominator "$Cp_{n+1}+Cp_{n-1}-2Cp_n$" is zero, the pixel specifying portion 41 does not select those three pixels (n−1), n, and (n+1) that produced this combination of simultaneous equations, but rather selects a combination of pixels comprising another three pixels (n'−1), n', and (n'+1) (for example, the pixels for n, (n+1), and (n+2), or the pixels for (n−2), (n−1), and n). Then the system of simultaneous equations of the aforementioned Equations (1) through (5) is solved for these other three pixels (n'−1), n', and (n'+1).

For the pixels that are specified as described above, the system of simultaneous equations can be solved, and the estimated direct radiation intensity $P_n$ that is calculated is used to calculate an average value for the estimated direct radiation intensities $P_n$ using the method described above. If the average value $P\hat{}$ of the estimated direct radiation intensities $P_n$ can be calculated, then the transmitted scattered radiation intensities $Sc_{n-1}$, $Sc_n$, and $Sc_{n+1}$ can also be calculated, as in the Equations (10) through (12), above, for the three pixels (n−1), n, and (n+1) that form the combination when the denominator "$Cp_{n+1}+Cp_{n-1}-2Cp_n$" is zero.

To summarize the explanation regarding the solving of the system of simultaneous equations, if the denominator "$Cp_{n+1}+Cp_{n-1}-2Cp_n$" is not zero, then each of the estimated direct radiation intensities $P_n$ ($=P_{n+1}=P_{n-1}$) is calculated using the equation (6), above, to calculate the average value $P\hat{}$. Substituting this average value $P\hat{}$ into the aforementioned Equations (10) through (12) enables the calculation of the transmitted scattered radiation intensities $Sc_{n-1}$, $Sc_n$, and $Sc_{n+1}$ when the denominator "$Cp_{n+1}+Cp_{n-1}-2Cp_n$" is not zero. Similarly substituting into the aforementioned Equations (10) through (12) enables the calculation of the transmitted scattered radiation intensities $Sc_{n-1}$, $Sc_n$, and $Sc_{n+1}$ even for the transmitted scattered radiation intensities $Sc_{n-1}$, $Sc_n$, and $Sc_{n+1}$ when the denominator "$Cp_{n+1}+Cp_{n-1}-2Cp_n$" is zero. In this way, first the estimated direct radiation intensities P are calculated when the denominator "$Cp_{n+1}+Cp_{n-1}-2Cp_n$" is not zero, and then, after calculating the average value $P\hat{}$, that value is used to calculate the transmitted scattered radiation intensities $Sc_{n-1}$, $Sc_n$, and $Sc_{n+1}$ when "$Cp_{n+1}+Cp_{n-1}-2Cp_n$" is not zero, and to calculate, similarly, the transmitted scattered radiation intensities $Sc_{n-1}$, $Sc_n$, and $Sc_{n+1}$ when the denominator "$Cp_{n+1}+Cp_{n-1}-2Cp_n$" is zero.

In this method, the test subject is the acrylic plate phantom Ph (which is a water cylinder phantom Ph in the second example of embodiment, described below), so the deviations in the estimated direct radiation intensity P are known, and the fact that they are smooth is used to calculate the estimated direct radiation intensities P (which is the average value $P\hat{}$ in the first example of embodiment) through performing smoothing and interpolation calculations on the estimated direct radiation intensities P calculated for the pixels specified initially by the pixel specifying portion 41 (that is, the "specified pixels"), or through calculating an average value for the estimated direct radiation intensities P. The smooth deviations in the estimated direct radiation intensities P and the averaging or the smoothing have the effect of reducing the variability due to statistical fluctuation error, making it possible to obtain a value that is nearer to the true values for the estimated direct radiation intensities P. The transmitted scattered radiation intensities Sc are calculated by substituting into the aforementioned Equations (2) through (4) these estimated direct radiation intensities P that are nearer to the true values, and because the averaging or smoothing/interpolation calculations are not performed on the transmitted scattered radiation intensities Sc themselves, there is the major benefit of having no loss of resolution in the transmitted scattered radiation intensities Sc. Moreover, it is possible to calculate accurately fine deviations in the transmitted scattered radiation intensities Sc due to deformations, or the like, in the grid foils, while maintaining the resolution for the transmitted scattered radiation intensities Sc.

As another method, when, for example, the denominator "$Cp_{n+1}+Cp_{n-1}-2Cp_n$" is not zero, then the transmitted scattered radiation intensities $Sc_{n-1}$, $Sc_n$, and $Sc_{n+1}$ are calculated prior to the estimated direct radiation intensities P, and the transmitted scattered radiation intensities $Sc_{n-1}$, $Sc_n$, and $Sc_{n+1}$ are calculated through interpolation of the transmitted scattered radiation intensities $Sc_{n-1}$, $Sc_n$, and $Sc_{n+1}$ when the denominator "$Cp_{n+1}+Cp_{n-1}-2Cp_n$" is zero, and the respective calculated transmitted scattered radiation intensities $Sc_{n-1}$, $Sc_n$, and $Sc_{n+1}$ are substituted into the aforementioned Equations (7) through (9), and when the denominator "$Cp_{n+1}+Cp_{n-1}-2Cp_n$" is not zero, the estimated direct radiation intensities P for when the denominator "$Cp_{n+1}+Cp_{n-1}-2Cp_n$" is zero are calculated, to calculate an average value $P\hat{}$ of the estimated direct radiation intensities $P_n$ for multiple combinations of three pixels (n−1), n, and (n+1) in the center portion of the grid 6, including those wherein the denominator "$Cp_{n+1}+CP_{n-1}-2Cp_n$" is zero. Additionally, this average value $P\hat{}$ is used and substituted into the aforementioned Equations (10) through (12) to calculate the transmitted scattered radiation intensities $Sc_{n-1}$, $Sc_n$, and $Sc_{n+1}$ again, where these recalculated transmitted scattered radiation intensities $Sc_{n-1}$, $Sc_n$, and $Sc_{n+1}$ may be used to calculate the deviation ratios Rcs in Step S5, described below.

[Step S5] Calculation/Interpolation of the Deviation Ratios

The deviation ratio calculating portion 46 uses the transmitted scattered radiation intensities Sc ($Sc_{n-1}$, $Sc_n$, and $Sc_{n+1}$), estimated by the intensity estimating portion 44, to calculate the deviation ratios Rcs. Specifically, with the transmitted scattered radiation intensities Sc as reference intensities, an average value $Sc\hat{}$, or a value $Sc_n\sim$ for each individual pixel, calculated through smoothing/interpolation calculations, are calculated for calculating the deviation ratios Rcs for each of the pixels relative to those values of the transmitted scattered radiation intensities Sc for all of the pixels. The ratios of the transmitted scattered radiation intensities $Sc_n$ for the individual pixels to the average value $Sc\hat{}$ or the $Sc_n\sim$ value for each individual pixel are defined as the deviation ratios Rcs, and when the deviation ratios Rcs for the individual pixels are defined as $Rcs_n$, then they are expressed by the following Equation (13):

$$Rcs_n = Sc_n/Sc\hat{}$$

or $$Rcs_n = Sc_n/Sc_n\sim \quad (13)$$

When calculating the deviation ratios for the transmitted scattered radiation, the reference scattered radiation intensity that is placed in the denominator corresponds to a scattered radiation intensity in the case of an ideal grid wherein the scattered radiation intensities are not affected by the installation conditions, as there is no deformation, or the like, in the foil.

The methods include:

1) Methods that simply uses an average value by approximating the distribution of the scattered radiation intensities as being uniform in two dimensions; and 2) Methods wherein the deviations in the scattered radiation intensity due to, for example, the shape of the phantom and the installation conditions, such as the peripheral portions of the grid, are given strict consideration, where the values that are used are obtained through two-dimensional smoothing/interpolation of the intensities of the scattered radiation estimated for the individual pixels, where the average value in 1, above, can be considered to be the simplest method of smoothing/interpolation calculations.

In this way, the deviation of the transmitted scattered radiation intensities Sc, considering the installation conditions of the grid 6 that arise because there are, for example, deformations in the absorbing foils 6a and 6b, are expressed as deviation ratios $Rcs_n$, through dividing by the reference values. The deviation ratios $Rcs_n$ are calculated by the deviation ratio calculating portion 46 for all pixels. After interpolation, if necessary, by the deviation ratio interpolating portion 47 of the deviation ratios $Rcs_{n-1}$, $Rcs_n$, and $Rcs_{n+1}$, calculated by the deviation ratio calculating portion 46, the results are sent again to the intensity estimating portion 44.

The deviation ratios Rcs, as with the direct radiation transmissivities Cp, as illustrated by the black-filled squares in FIG. 7, will vary for each discrete distance $L_{s+1}$, $L_{s+2}$, $L_{s+3}$, . . . . The deviation ratios Rcs that have been calculated by the deviation ratio calculating portion 46 undergo interpolation processing by the deviation ratio interpolating portion 47 for distances before and after the discrete distances $L_{s+1}$, $L_{s+2}$, $L_{s+3}$, . . . . The interpolation results are, for example, as illustrated by the dotted line in FIG. 7. For the method for the interpolation, values obtained through the arithmetic mean (additive mean) or the geometric mean for deviation ratios Rcs for mutually adjacent discrete distances (for example, Ls+1 and Ls+2) may be calculated as the deviation ratios Rcs for a distance between the aforementioned adjacent discrete distances, Legrange interpolation may be performed, a value corresponding to a distance on the dotted line produced through the linear approximation in FIG. 7 using the least-squares method may be calculated as the deviation ratios Rcs, and so forth, and there is no particular limitation insofar as the method is a commonly used interpolation method.

[Step S6] Actual Measurement with the Actual Test Subject Present

Following this, x-ray radiography is performed with another test subject M that is different from the test subject M used in Step S3 through S5 (which, in this case, was the phantom Ph). As illustrated in FIG. 1, the test subject M that is used in the actual x-ray radiography is used. The actual test subject M is interposed between the x-ray tube 2 and the grid 6, and the x-rays from the x-ray tube 2 are emitted towards the grid 6 and the FPD 3, to perform the x-ray radiography in a state wherein the actual test subject M is present, to thereby perform the measurement in the state wherein the actual test subject M is present. That is, the x-ray tube 2 emits x-rays in a state wherein the actual test subject M is present (the test subject M that is used in the actual x-ray radiography), to cause incidence on the FPD 3 through the grid 6, so that the actual measured intensities G, which are the intensities after transmission through the grid 6 in the actual measurement in the state wherein the test subject M is present, are obtained in the same manner as in Step S3. Specifically, the detecting elements d of the FPD 3 (illustrated in FIG. 3) convert the x-rays into electric signals to read out the x-rays in the state wherein the test subject M is present, to convert into pixel values in accordance with the electric signals.

[Step S7] Estimation/Interpolation of Intensities

As described also for Step S4, the pixel values are equal to the actual measured intensities G, which are the intensities after transmission through the grid 6 in the actual measurement in the state wherein the test subject M is present. Similarly, the pixel specifying portion 41 specifies three adjacent pixels (n−1), n, and (n+1) as a combination of three pixels. Then the intensity estimating portion 44 again estimates the transmitted scattered radiation intensities Sc and the estimated direct radiation intensities P for the three adjacent pixels (n−1), n, and (n+1) that were specified by the pixel specifying portion 41, based on the deviation ratios Rcs calculated by the deviation ratio calculating portion 46, the deviation ratios Rcs interpolated by the deviation ratio interpolating portion 47, the direct radiation transmissivities Cp calculated by the transmissivity calculating portion 42, the direct radiation transmissivities Cp interpolated by the transmissivity interpolating portion 43, and the actual measured intensities G, which are equal to the pixel values from the FPD 3.

In the same manner as in Step S4, the system of simultaneous equations is solved to estimate the transmitted scattered radiation intensities Sc and the estimated direct radiation intensities P; however, the part that is different from Step S4 is the point that the deviation ratio Rcs parameters are taken into consideration, and the point that there are differences in the equation regarding the transmitted scattered radiation intensities Sc and the equations regarding the estimated direct radiation intensities P. Note that the explanations are omitted for the places that are the same as in Step S4.

In Step S7, the transmitted scattered radiation intensities Sc are the transmitted scattered radiation intensities wherein the installation conditions are of the ideal case wherein there are no nonuniformities in the foils, such as deformation of the absorbing foils in the grid 6. If the deviation ratios that are produced due to nonuniformities in the grid 6 were eliminated, then the transmitted scattered radiation intensities Sc would vary smoothly in the case wherein the test subject was a water column (such as a water cylinder), a human body, or the like, and wherein the radiation was x-rays or γ-rays, and thus could be expressed by the following Equation (1)″, which assumes that the three adjacent pixels are all equal:

$$Sc_{n-1} = Sc_n = Sc_{n+1} \quad (1)''$$

The aforementioned Equation (1)″ corresponds to Equation (A)″ in the present invention. The actual measured intensities G are expressed by the system of simultaneous equations (2)″ through (4)″, for each of the three adjacent pixels (n−1), n, and (n+1), wherein the actual measured intensity G is defined as equal to the sum of the product of the transmitted scattered radiation intensity Sc· deviation ratios Rcs added to the product of the estimated direct radiation intensity P· direct radiation transmissivity Cp:

$$G_{n+1} = P_{n+1} \cdot Cp_{n+1} + Sc_{n+1} \cdot Rcs_{n+1} \quad (2)''$$

$$Gn = P_n \cdot Cp_n + Sc_n \cdot Rcs_n \quad (3)''$$

$$G_{n-1} = P_{n-1} \cdot Cp_{n-1} + Sc_{n-1} \cdot Rcs_{n-1} \quad (4)''$$

Equation (2)'' corresponds to Equation (B-1)'' in the present invention, Equation (3)'' corresponds to Equation (B-2)'' in the present invention, and Equation (4)'' corresponds to Equation (B-3)'' in the present invention.

The estimated direct radiation intensities P for the individual pixels will vary depending on the shape, material, etc., of the test subject M, in contrast to the case of the acrylic plate phantom Ph in Step S3, where the deviation is expressed by an interpolation calculation for the estimated direct radiation intensities P of the adjacent pixels. In the present first example of embodiment, the variation in the estimated direct radiation intensities P within the three adjacent pixels of (n−1), n, (n+1) can be approximated through a linear approximation as in Equation (5)'', below.

$$P_n = (P_{n+1} + P_{n-1})/2 \quad (5)''$$

Equation (5)'' corresponds to Equation (C)'' in the present invention. Additionally, in terms of the interpolation method for the estimated direct radiation intensities P, Legrange interpolation, for example, may be used in the same manner as described for the interpolation of the direct radiation transmissivities Cp, or the transmitted scattered radiation intensities Sc in Step S4, and there is no particular limitation to the aforementioned Equation (5)'' insofar as the interpolation is that which is commonly used.

The estimated direct radiation intensities $P_{n-1}$, $P_n$, and $P_{n+1}$, and transmitted scattered radiation intensities $Sc_n$ ($=Sc_{n+1}=Sc_{n-1}$) can be calculated as in Equations (6)'' through (9)'' by solving the system of simultaneous equations obtained from Equations (1)'' through (5)'', as described above:

$$Sc_n = G_{n+1}/Rcs_{n+1} - \{(Cp_n \cdot Rcs_{n-1} - 2Cp_{n-1} \cdot Rcs_n) \cdot G_{n+1} + 2Cp_{n-1} Rcs_{n+1} \cdot G_n - Cp_n \cdot Rcs_{n+1} \cdot G_{n-1}\}/(Cp_{n+1} \cdot Cp_n \cdot Rcs_{n+1} \cdot Rcs_{n-1} - 2Cp_{n+1} \cdot Cp_{n-1} \cdot Rcs_{n+1} \cdot Rcs_n + Cp_n \cdot Cp_{n-1} \cdot Rcs_{n+1}^2) \quad (6)''$$

$$P_{n-1} = \{(Cp_n \cdot Rcs_{n-1} - 2Cp_{n-1} \cdot Rcs_n) \cdot G_{n+1} + 2Cp_{n-1} \cdot Rcs_{n+1} \cdot G_n - Cp_n \cdot Rcs_{n+1} \cdot G_{n-1}\}/(Cp_{n+1} \cdot Cp_n \cdot Rcs_{n+1} - 2Cp_{n+1} \cdot Cp_{n-1} \cdot Rcs_n + Cp_n \cdot Cp_{n-1} \cdot Rcs_{n+1}) \quad (7)''$$

$$P_n = G_n/Cp_n - Rcs_n \cdot [G_{n+1}/Rcs_{n+1} - \{(Cp_n \cdot Rcs_{n-1} - 2Cp_{n-1} \cdot Rcs_n) \cdot G_{n+1} + 2Cp_{n-1} \cdot Rcs_{n+1} \cdot G_n - Cp_n \cdot Rcs_{n+1} \cdot G_{n-1}\}/(Cp_{n+1} \cdot Cp_n \cdot Rcs_{n+1} \cdot Rcs_{n-1} - 2Cp_{n+1} \cdot Cp_{n-1} \cdot Rcs_{n+1} \cdot Rcs_n + Cp_n \cdot Cp_{n-1} \cdot Rcs_{n+1}^2)] \quad (8)''$$

$$P_{n+1} = G_{n+1}/Cp_{n+1} - Rcs_{n-1} \cdot [\{(Cp_n \cdot Rcs_{n-1} - 2Cp_{n-1} \cdot Rcs_n) \cdot G_{n+1} + 2Cp_{n-1} \cdot Rcs_{n+1} \cdot G_n - Cp_n \cdot Rcs_{n+1} \cdot G_{n-1}\}/(Cp_{n+1} \cdot Cp_n \cdot Rcs_{n+1} \cdot Rcs_{n-1} - 2Cp_{n+1} \cdot Cp_{n-1} \cdot Rcs_{n+1} \cdot Rcs_n + Cp_n \cdot Cp_{n-1} \cdot Rcs_{n+1}^2)] \quad (9)''$$

The estimated direct radiation intensities $P_{n-1}$, $P_n$, and $P_{n+1}$, and the transmitted scattered radiation intensities $Sc_n$ ($=Sc_{n+1}=Sc_{n-1}$), calculated using the aforementioned equations (6)'' through (9)'' are values that are calculated when the denominators included in the solution for the system of simultaneous equations of the aforementioned Equations (1)'' through (5)'' are not zero.

When the denominators included in the solution to the system of simultaneous equations of Equations (1)'' through (5)'' are zero, then it will not be possible to solve the system of simultaneous equations of the aforementioned Equations (1)'' through (5)'', and thus for the three pixels (n−1), n, (n+1) that setup the combination when the denominator is zero, the estimation cannot be made because it is not possible to calculate the estimated direct radiation intensities $P_{n-1}$, $P_n$, and $P_{n+1}$, or the transmitted scattered radiation intensities $Sc_{n-1}$, $Sc_n$, and $Sc_{n+1}$ there are, for example, two methods, method 1), and method 2), below, as methods for estimating the estimated direct radiation intensities $P_{n-1}$, $P_n$, and $P_{n+1}$, and the transmitted scattered radiation intensities $Sc_{n-1}$, $Sc_n$, and $Sc_{n+1}$, in the case of three pixels (n−1), n, (n+1) that form a combination when the denominator is zero:

Method 1) is a method wherein the transmitted scattered radiation intensities Sc are calculated first. Because the transmitted scattered radiation intensities Sc are for of the ideal case for the installation conditions wherein there is no deformation in the absorbing foils in the grid 6, first the plurality of transmitted scattered radiation intensities $Sc_n$ obtained when the denominator is not zero is used to calculate transmitted scattered radiation intensities $Sc_n$~ for all pixels through appropriate smoothing/interpolation calculations, including pixels which have not yet been obtained because the denominator is zero. As described for the aforementioned Equation (1)'', when the test subject is a water column (such as a water cylinder) or a human body, or the like, and the emitted radiation is x-rays or γ-rays, the change is smooth and smoothing has the effect of reducing variability due to statistical fluctuation error, producing a value $Sc_n$~ that is near to the true value for the transmitted scattered radiation intensity $Sc_n$. The transmitted scattered radiation intensities $Sc_n$~ obtained in this way, are substituted for the $Sc_n$ in Equation (3), above for all pixels to calculate directly the estimated direct radiation intensity. In this method, as described above, smoothing/interpolation calculations are not performed for the estimated direct radiation intensities P for those values from pixels wherein the denominator is not zero, and thus there is a major benefit in not degrading the resolution of the image of the estimated direct radiation intensities P.

The method in 2) is a method wherein interpolation is performed, in the same manner as in Equation (5)'', above, between the estimated direct radiation intensities $P_{n-1}$, $P_n$, and $P_{n+1}$, obtained already in Equations (7)'' through (9)'', above, to interpolate the estimated direct radiation intensities $P_{n-1}$, $P_n$, and $P_{n+1}$ that have not yet been obtained. That is, the intensity interpolating portion 45 interpolates the estimated direct radiation intensities $P_{n-1}$, $P_n$, and $P_{n+1}$, which were estimated by the intensity estimating portion 44. In regards to this interpolation as well, there is no particular limitation to the aforementioned Equation (5)'', insofar as a commonly used interpolation is used. The estimated direct radiation intensities $P_{n-1}$, $P_n$, and $P_{n+1}$, interpolated by the intensity interpolating portion 45, are sent to the display unit 5, and the like.

In this way, in the same manner as in Step S4, the transmitted scattered radiation intensities $Sc_n$ may be calculated first, or the estimated direct radiation intensities $P_n$ may be calculated first, as described above.

In this way, going through the steps S1 through S7 and using, as the pixel values, the estimated direct radiation intensities $P_n$ calculated in Step S7 makes it possible to obtain appropriately an x-ray image wherein scattered radiation and false images due to the grid 6 are reduced. The x-ray images may be displayed on the display unit 5, described above, may be written to and stored on a memory medium such as typified by a random access memory (RAM) to be read out as appropriate when necessary, and may be printed out using printing means such as typified by a printer. Furthermore, in Method 1 in Step S7, if the transmitted scattered radiation intensities $Sc_n$ are calculated prior to the estimated direct radiation transmission intensities $P_n$, later, after the estimated direct radiation intensities $P_n$ have been calculated, they may be outputted, as an x-ray image, to the display unit 5, the memory medium, the printing means, or the like.

Additionally, because the direct radiation transmissivities Cp are calculated for each distance SID from the focal point of the x-ray tube 2 to the detecting surface of the FPD 3, the parameters calculated in steps S3 through S7 are values that can be obtained appropriately for each distance SID. Given this, even if the distance SID were to be varied, insofar as the distance between the test subject M and the FPD 3 has not changed, there will be little change in the scattered radiation distribution, in contrast to the case for the direct radiation transmissivities Cp, making it possible to essentially ignore changes in the deviation ratios $Rcs_n$ of the transmitted scattered radiation intensities Sc. In this case, if the deviation ratios $Rcs_n$ at a given SID are calculated in advance, then those values can be used also for a different distance SID, making it possible to omit Steps S3 through S5. Given this, Step S6 and beyond, starting with the actual measurement in the state wherein the actual test subject M is present, should be performed. Furthermore, in a case wherein the change in the deviation ratio $Rcs_n$ relative to a change in the distance SID cannot be ignored, then if the deviation ratios $Rcs_n$ are stored in advance for each discrete distance $L_{s+1}$, $L_{s+2}$, $L_{s+3}$, ..., and interpolation calculations are performed for the actual distances SID, then, of course, Step S3 through S5 can be omitted. Then Step S6 and beyond should be performed for the actual measurement in a state wherein the actual test subject M is present. Consequently, in actual x-ray radiography, even if there is a change in the distance SID, as illustrated in FIG. 6, the direct radiation transmissivities Cp and deviation ratios Rcs of the transmitted scattered radiation intensities Sc that take into account each distance SID can be used to enable application to cases such as circulation system imaging devices wherein imaging is performed while varying the distances between the x-ray tube 2, the grid 6, and the FPD 3.

In the x-ray radiography device as set forth in the first example of embodiment, x-rays are emitted by the x-ray tube 2, and are incident on an FPD 3 through a grid 6. A portion of the scattered x-rays (scattered radiation) is removed by the grid 6, and the FPD 3 detects the x-rays to produce an x-ray image. At this time, of the various pixels that structure the x-ray image, particular pixels are specified by a pixel specifying portion 41. An intensity estimating portion 41 estimates the scattered x-ray intensity (scattered radiation intensity) at the particular pixels specified by the pixel specifying portion 41, and/or the direct x-ray intensity (direct radiation intensity) at the particular pixels. Consequently, it is possible to estimate appropriately the scattered x-ray intensity and/or the direct x-ray intensity at the particular pixels, taking into account the state of installation of the grid 6.

On the other hand, the following is performed for those pixels that are not specified. An intensity interpolating portion 45 interpolates the scattered x-ray intensities of pixels that are not specified and/or the direct x-ray intensities of pixels that are not specified, based on the scattered x-ray intensities and/or direct x-ray intensities estimated by the intensity estimating portion 44. Consequently, intensities are estimated by the intensity estimating portion 44 for specified pixels, and intensities are interpolated by the intensity interpolating portion of 45 for the pixels that are not specified. Given this, x-ray images can be obtained appropriately based on these x-ray intensities, and x-ray images can be obtained for only the direct x-rays (direct radiation) by completely removing scattered radiation, including scattered x-rays (scattered radiation) that are transmitted through the grid 6, while eliminating the shadow of the grid 6. The x-ray images obtained through these pixel specifying portion 41, intensity estimating portion 44, and intensity interpolating portion 45 can be applied independently of a specific grid (for example, the synchronized grid 6 such as in the first example of embodiment), in any type of scattered radiation removing means. The result is applicability also to general-use scattered radiation removing means, and the ability to obtain appropriate x-ray images independently of the status of installation of the scattered radiation removing means, as typified by the grid 6. Furthermore, it is not necessary to estimate the intensity for all pixels, but rather the intensity may be estimated for only specified particular pixels, and interpolation may be performed for the intensities for the remaining non-specified pixels, and thus there are also the effects of being able to reduce and shorten the calculation processes.

Additionally, in method 1 in Step S7, the $Sc_n \sim$ values are calculated through smoothing/interpolation calculations from the transmitted scattered radiation intensities $Sc_n$ for the specified pixels, and this has the effect of not only smoothing the variations in the transmitted scattered radiation intensities, as described above, but the averaging or smoothing also has the effect of reducing variability due to statistical fluctuation error, so that transmitted scattered radiation intensities $Sc_n \sim$ that are closer to the true values are obtained. The transmitted scattered radiation intensities $Sc_n \sim$ that are closer to the true values are substituted for $Sc_n$ in Equation (3) to calculate the estimated direct radiation intensities P, where the smoothing/interpolation calculations are not performed from the values of the pixels wherein the denominator is not zero, for the estimated direct radiation intensities P, and thus there is the major benefit of not degrading the resolution in the image of the estimated direct radiation intensities P. Furthermore, this enables the resolution of the estimated direct radiation intensities P to be maintained, making it possible to calculate with precision fine variations in the estimated direct radiation intensities P relative to fine changes in the shape and material of the test subject.

The specific effect of being able to obtain an appropriate x-ray image independently of the status of installation of the grid 6 is applicable even if there is an overall misalignment of the grid 6 to a row of pixels or to a column of pixels, and even if there is a misalignment due to deformation of the individual absorbing foils 6a and 6b that structure the grid 6. Furthermore, even if there is a misalignment due to deformation of the absorbing foils 6a and 6b that structure the grid 6, and even if the scattered radiation from the test subject M is an angular distribution, it is still possible to calculate the intensities (for example, the estimated direct radiation intensities P) for all of the pixels. This is because not only are the direct radiation transmissivities Cp by the grid taken into account for all of the pixels, but also the transmitted scattered radiation intensities Sc and the deviation ratios Rcs thereof are also taken into account.

Additionally, it is not necessary to estimate the intensities for all of the pixels, but rather estimations are performed for only specified particular pixels, and interpolation is performed for the intensities for the remaining non-specified pixels, thus making it possible to reduce the calculation processes and reduce the time, as described above, without the error in the scattered radiation distribution through smoothing, and the like, that would occur if the deviation ratios Rcs of the transmitted scattered radiation intensities $Sc_n$ were not taken into account, conversely, producing false images.

Additionally, the present invention can be applied also when there are changes in the positions of the x-ray tube 2, the grid 6, and the FPD 3, and even when misalignment due to deformation of the absorbing foils 6a and 6b causes the shadows of the absorbing foils 6a and 6b to not be contained within the same pixel rows and pixel columns. As described above, the present invention can also be applied to cases wherein imaging is performed with the distances between the x-ray tube 2, the grid 6, and the FPD 3 changing each time, as in circulation system imaging devices, and the like. Furthermore, it is not necessary to set the conditions for the tolerances for the misalignment through deformation of the absorbing foils 6a and 6b, which has a major effect in terms of cost reduction and in technical ease.

Additionally, it is possible to compensate for the effect of misalignment, along with the effect of an angular distribution of the scattered radiation from the test subject M in the tolerance values for the misalignment due to deformation of the absorbing foils 6a and 6b, and thus it is possible to determine tolerance values in conjunction with practical mechanical strengths and assembly precision. Consequently, there is a large effect in terms of cost reductions and technical ease, as with the previous paragraph.

In the first example of embodiment, as the scattered radiation removing means, a synchronized cross grid 6 was used wherein the layout direction of the absorbing foils 6a and 6b, which absorb the scattered radiation, are essentially parallel to the row direction and column direction of the detecting elements d, and the spacings $K_{gy}$ and $K_{gx}$ between mutually adjacent absorbing foils 6a and 6b layers are multiple integers (illustrated as 2 in FIG. 3) of the spacings $K_{fy}$ and $K_{fx}$ between mutually adjacent pixels. In this type of synchronized grid, the offsets between the absorbing foils 6a and 6b and pixels of other layers (middle layers 6c) have periodicity that matches that of between the individual pixels, and thus the calculations can be performed regularly and periodically. Consequently, the processes are simple, the calculation processing is simplified, and the calculation processing is made shorter. The result is not only the ability to estimate the intensities simply, but also to interpolate the intensities.

Furthermore, as described above, there is also the effect of being able to predict, from geometric simulations, rather than just from transmissivities of the direct radiation for the individual pixels (the direct radiation transmissivities Cp) and from the deviation ratios Rcs obtained through actual measurements, the particular pixels that form combinations wherein the absolute values in the denominators included in the solution to the system of simultaneous equations described above will be equal to or less than a particular value ("0" in the first example of embodiment), enabling pixels that form combinations that will be greater than that particular value to be set, even when there are changes in the distances between the x-ray tube 2, the grid 6, and the FPD 3.

Preferably, x-ray radiography is performed in advance, in a state wherein the test subject not present, to calculate the transmissivities in advance. That is, actual measurement data can be obtained in a state wherein the test subject not present through x-rays are emitted from the x-ray tube 2, in a state wherein the test subject not present, to be incident on the FPD 3 through the grid 6. A transmissivity calculating portion 42 is provided for calculating the direct radiation transmissivities Cp, which are the ratios of transmission of the direct radiation before transmission through the grid 6 and after transmission through the grid 6, calculated through actual measurements in a state wherein the test subject not present. The provision of this type of transmissivity calculating portion 42 enables the calculation of direct radiation transmissivities Cp.

When the distances between the x-ray tube 2, the grid 6, and the FPD 3 will vary, then the transmissivity calculating portion 42, described above, will calculate the direct radiation transmissivities Cp for discrete distances between the x-ray tube 2, the grid 6, and the FPD 3, and, more preferably, a transmissivity interpolating portion 43 is provided for interpolating the direct radiation transmissivities Cp for distances before and after the aforementioned discrete differences, based on the direct radiation transmissivities Cp calculated by the transmissivity calculating portion 42. The provision of the transmissivity calculating portion 42 and the transmissivity interpolating portion 43 in this way enables the direct radiation transmissivities Cp to be calculated in accordance with the distances, even when there are changes in the distances between the x-ray tube 2, the grid 6, and the FPD 3.

Additionally, the estimated direct radiation intensities P can be calculated accurately for all pixels by taking into account and using the transmissivities of the direct radiation (the direct radiation transmissivities Cp) for all pixels, including those wherein there is also attenuation through absorption of the direct radiation by the grid cover 6d and the middle material, rather than just those pixel rows or pixel columns that are blocked by the absorbing foils 6a and 6b.

These direct radiation transmissivies Cp are applied to the x-ray radiography in the state wherein the actual test subject M (the phantom Ph in the first example of embodiment) is present. That is, the x-ray tube 2 emits x-rays in a state wherein the actual phantom Ph is present, and the x-rays are incident on to the FPD 3 through the grid 6, to produce actual measured intensities G that are the intensities after transmission through the grid 6 in an actual measurement in the state wherein the phantom Ph is present. The intensity estimating portion 44 estimates the intensities for the particular pixels, specified by the pixel specifying portion 41, based on the direct radiation transmissivities Cp calculated by the transmissivity calculating portion 42 or the direct radiation transmissivities Cp interpolated by the transmissivity interpolating portion 43, and on the actual measured intensities G, described above, from the actual measurement in the state wherein the phantom Ph is present. In this way, it is possible to calculate the direct radiation transmissivities Cp based on the actual measurement data, in a state wherein the test subject not present, and to use these direct radiation transmissivities Cp to estimate intensities based on the actual measured intensities G in the state wherein the phantom Ph is present.

Specifically, the intensity estimating portion 44, when estimating unknown intensities for particular pixels that are specified by the pixel specifying portion 41, determines a number of particular pixels to be specified by the pixel specifying portion 41 in accordance with the number of unknowns, which are unknown direct radiation transmissivities and the number of knowns, which are known actual measured intensities G, and the intensity estimating portion 44 estimates the intensities by solving a system of simultaneous equations pertaining to the actual measured intensities G, the direct radiation transmissivities Cp, and the intensities to be estimated, for each of the particular pixels that have been determined. The intensities can be estimated easily through solving this type of system of simultaneous equations.

The transmitted scattered radiation intensities Sc and the estimated direct radiation intensities P can be estimated easily through solving the system of simultaneous equations obtained from Equations (1) through (5), above. Additionally, this type of system of simultaneous equations is useful in the case wherein the transmissivity thickness for the direct radiation is uniform, or in other words, when the estimated direct radiation intensities P are all identical values for every pixel, for example, when an acrylic plate phantom Ph is used as the test subject M.

Preferably, x-ray radiography is performed in advance in a state wherein the test subject not present, to calculate in advance the direct radiation transmissivities Cp, following which x-ray radiography is performed in a state wherein a test subject M is present (such as, for example, an acrylic plate phantom Ph or a water cylinder phantom Ph), to calculate deviation ratios Rcs for each individual pixel relative to a reference value or reference values (an average value, or a value for each individual pixel calculated through smoothing/interpolation calculations) for all of the pixels pertaining to the intensities. In other words, the x-ray tube 2 emits x-rays in a state wherein a phantom Ph is present, and the x-rays are caused to pass through the grid 6 to be incident on the FPD 3, to produce intensities that are estimated by the intensity estimating portion 44 based on actual measurements in the state wherein the phantom Ph is present. A deviation ratio calculation portion 46, for calculating the deviation ratios Rcs, described above, based on those intensities, is provided, where the deviation ratios Rcs calculated by the deviation ratio calculating portion 46 are applied to the x-ray radiography for another test subject M (the test subject M that is used in the actual x-ray radiography).

When there are to be changes in the distances between the x-ray tube 2, the grid 6, and the FPD 3, the aforementioned deviation ratio calculating portion 46 calculates the deviation ratios for discrete distances between the x-ray tube 2, the grid 6, and the FPD 3, and, more preferably, a deviation ratio interpolating portion 47 is provided for interpolating the deviation ratios for distances before and after the aforementioned discreet distances. The provision of the deviation ratio calculating portion 46 and the deviation ratio interpolating portion 47 in this way enables the deviation ratios to be calculated in accordance with the distances, even when there are changes in the distances between the x-ray tube 2, the grid 6, and the FPD 3.

The x-ray tube 2 emitting x-rays in a state wherein the another test subject M is present (where at this point this is the test subject M that is used in the actual x-ray radiography), and causing the x-rays to pass through the grid 6 to be incident on the FPD 3 enables actual measured intensities G, which are the intensities after transmission through the grid 6 in the actual measurement in the state wherein the test subject M is present, to be obtained. The intensity estimating portion 44 estimates the intensities of the particular pixels specified by the pixel specifying portion 41 based on the deviation ratios Rcs calculated by the deviation ratio calculation portion 46, the deviation ratios Rcs interpolated by the deviation ratio interpolating portion 47, the direct radiation transmissivities Cp calculated by the transmissivity calculating portion 42, the direct radiation transmissivities Cp interpolated by the transmissivity interpolating portion 43, and the actual measured intensities G, described above, in the actual measurement in the state wherein the other test subject M (the test subject M used in the actual x-ray radiography) is present. In this way, the direct radiation transmissivities Cp are calculated based on actual measurement data in a state wherein the test subject not present, and those direct radiation transmissivities can be used to calculate deviation ratios Rcs by performing x-ray radiography in a state wherein an the test subject M (which, at this point, is the phantom) is present, where the deviation ratios Rcs or deviation ratios the that is interpolated by the deviation ratio interpolating portion 47, can be used to perform x-ray radiography in a state wherein another test subject M (which, at this point, is the test subject M that is used in the actual x-ray radiography) is present, to estimate the intensities based on the actual measured intensities G in the state wherein the test subject M (the test subject M used in the actual x-ray radiography) is present.

Specifically, when the intensity estimating portion 44 estimates unknown intensities for particular pixels specified by the pixel specifying portion 41, the pixel specifying portion 41 determines a number of particular pixels to be specified in accordance with the number of knowns of the known deviation ratios Rcs, the number of knowns of the known direct radiation transmissivities Cp, and the number of knowns of the actual measured intensities G, and the intensity estimating portion 44 estimates the intensities by solving a system of simultaneous equations pertaining to the actual measured intensities G, the deviation ratios Rcs, the direct radiation transmissivities Cp, and the intensities to be estimated, for each particular pixels that has been determined. The intensities can be estimated easily by solving this type of system of simultaneous equations.

The transmitted scattered radiation intensities Sc and the estimated direct radiation intensities P can be estimated easily through solving the system of simultaneous equations obtained from the aforementioned Equations (1)" through (5)".

A second example of embodiment according to the present invention will be explained next in reference to the drawings. FIG. 9 is a diagram illustrating schematically x-ray radiography in a state wherein a test subject is present pertaining to a second example of embodiment in a case wherein a water cylinder phantom is used as the test subject. Note that those places that are the same as in the first example of embodiment, described above, are assigned identical codes, and not only are explanations thereof omitted, but drawings thereof are omitted as well. The same x-ray radiography device is used in the second example of embodiment as in the first example of embodiment (illustrated in FIG. 1), the same FPD 3 is used as in the first example of embodiment (illustrated in FIG. 2), and the same synchronized cross grid 6 is used as in the first example of embodiment (illustrated in FIG. 3).

Additionally, in the second example of embodiment, the structure and data flow in the specific image processing unit 4 is identical to that in the first example of embodiment (illustrated in FIG. 4), and the actual x-ray radiography assumes the same flow as in the first example of embodiment (illustrated in FIG. 5). The points of difference from the first example of embodiment are in the actual measurement in the state wherein the phantom is present in Step S3 (illustrated in FIG. 5), where, in the first example of embodiment, described above, the phantom Ph was an acrylic plate, as illustrated in FIG. 8, where, in contrast, in the second example of embodiment the phantom Ph, as illustrated in FIG. 9, is a water cylinder. Consequently, explanations are omitted for the flow aside from Step S3 and Step S4, related thereto.

[Step S3] Actual Measurement in a State Wherein a Phantom is Present

X-ray radiography is performed in a state wherein the test subject M is present. As is illustrated in FIG. 9, a phantom Ph which is near to the actual test subject M is used as the test subject M. For example, if the goal is to perform imaging of the torso of a human body, a water cylinder phantom Ph, having a transmissivity essentially the equivalent to that of the torso of the human body, is used as the test subject M. The actual measured intensities G are obtained in the same manner as in the first example of embodiment through the actual measurement in this Step S3.

[Step S4] Estimating/Interpolating the Intensities

The actual measured intensities G are obtained through the actual measurements in Step S3, and thus are known. The direct radiation transmissivities Cp are obtained through the actual measurements in Step S1, and are calculated/interpolated in Step S2, and thus are known. While the estimated direct radiation intensities P themselves are yet unknown, if a known phantom Ph is used, then, for each set of three adjacent pixels (n−1), n, and (n+1), the estimated direct radiation distribution P(n−1), P(n), and P(n+1) is known when the estimated direct radiation distribution is defined as P(n−1), P(n), and P(n+1). When the water cylinder phantom Ph is placed directly above the center of the FPD 3, the distance from the center of the FPD 3 is defined as x, the x-ray intensity prior to transmission is defined as $I_0$, the estimated direct radiation distribution P(x) at a distance of x from the center of the FPD 3, or in other words, the x-ray intensity after transmission at a distance of x, is defined as $I_x$, the attenuation rate in water is defined as $\mu H_2O$, and the transmission length that is the length of transmission of the x-rays through the water cylinder is defined as L, then the estimated direct radiation distribution P(x) at a distance of x (which is equal to the x-ray intensity $I_x$ after transmission, at the distance x) is represented by Equation (14), below:

$$P(x)=I_x=I_0 \cdot \exp(-\mu H_2O \cdot L) \qquad (14)$$

Because the estimated direct radiation distribution P(x) that is obtained through Equation (14), above, is already known, the estimated direct radiation distributions P(n−1), P(n), and P(n+1) for each of the three pixels (n−1), n, and (n+1) are already known. The estimated direct radiation intensities P that will ultimately be estimated are already known, where the estimated direct radiation intensities P are expressed as the product of the known estimated direct radiation distributions P(n−1), P(n), and P(n+1), and conversion factors thereof. If the conversion factors are defined as $a_n$, those conversion factors are, of course, unknown. In this way, the estimated direct radiation intensities $P_{n-1}$, $P_n$, and $P_{n+1}$ in Equations (2) through (4) used in the first example of embodiment are, respectively, expressed as $P_{n+1}=a_n \cdot P(n+1)$, $P_n=a_n \cdot P(n)$, and $P_{n-1}=a_n \cdot P(n-1)$. The combined equations with the aforementioned Equations (2) through (4) that were used in the first example of embodiment are expressed as the system of equations (2)′ through (4)′.

Note that as in the first example of embodiment, described above, in the second example of embodiment, the deviations in the transmitted scattered radiation intensity Sc between the three adjacent pixels (n−1), n, and (n+1) can be approximated through the linear approximation as in Equation (1), below:

$$Sc_n=(Sc_{n+1}+Sc_{n-1})/2 \qquad (1).$$

Equation (1), above, corresponds to Equation (A) in the present invention. Additionally, this Equation (1) is identical to the Equation (1) discussed in the first example of embodiment. An actual measured intensity G is equal to the sum of the transmitted scattered radiation intensity Sc and the product of the estimated direct radiation intensity P· direct radiation transmissivity Cp, and is expressed by the system of simultaneous equations (2) through (4) for each of the three adjacent pixels (n−1), n, and (n+1):

$$G_{n+1}=a_n \cdot P(n+1) \cdot Cp_{n+1}+Sc_{n+1} \qquad (2)'$$

$$G_n=a_n \cdot P(n) \cdot Cp_n+Sc_n \qquad (3)'$$

$$G_{n-1}=a_n \cdot P(n-1) \cdot Cp_{n-1}+Sc_{n-1} \qquad (4)'$$

Equation (2)′ corresponds to Equation (B-1)′ in the present invention, Equation (3)′ corresponds to Equation (B-2)′ in the present invention, and Equation (4)′ corresponds to Equation (B-3)′ in the present invention.

The conversion factors $a_n$ and the transmitted scattered radiation intensities $Sc_{n-1}$, $Sc_n$, and $Sc_{n+1}$ are calculated through the following Equations (6)′ through (9)′ through solving the system of simultaneous equations obtained through Equation (1) and Equation (2)′ through (4)′, as described above:

$$a_n=(G_{n+1}+G_{n-1}-2G_n)/\{P(n+1) \cdot Cp_{n+1}+P(n-1) \cdot Cp_{n-1}-2P(n) \cdot Cp_n\} \qquad (6)'$$

$$Sc_{n+1}=G_{n+1}-a_n \cdot P(n+1) \cdot Cp_{n+1} \qquad (7)'$$

$$Sc_n=G_n-a_n \cdot P(n) \cdot Cp_n \qquad (8)'$$

$$Sc_{n-1}=G_{n-1}-a_n \cdot P(n-1) \cdot Cp_{n-1} \qquad (9)'$$

In the aforementioned Equations (6)′ through (9)′, first the conversion factors $a_n$ are calculated in Equation (6)′ using the known actual measured intensities $G_{n-1}$, $G_n$, and $G_{n+1}$ and the known direct radiation transmissivities $Cp_{n-1}$, $Cp_n$, and $Cp_{n+1}$, and after these conversion factors $a_n$ are known, these known conversion factors $a_n$ also used to calculate the respective transmitted scattered radiation intensities $Sc_{n-1}$, $Sc_n$, and $Sc_{n+1}$ using Equations (7)′ through (9)′.

When, in this way, the combination of the three adjacent pixels (n−1), n, and (n+1) is defined as a set, then a single conversion factor $a_n$ is obtained for each individual set; however, actually the conversion factors $a_n$ should be identical values for a the entire set for a combination of three pixels. However, in practice, each is slightly different at the peripheral portion of the grid 6, as also discussed in the first example of embodiment, above, and there will be differences through statistical fluctuation error. An average value may be taken for the conversion factors $a_n$ in order to reduce the impact of the installation status of the grid 6 and of statistical fluctuation errors. For example, in the case wherein there are minor differences in the portions surrounding the grid 6, as described above, then the individual conversion factors $a_n$ can be calculated in the combination of the three pixels (n−1), n, and (n+1) in the center portion of the grid 6, and the average value $\hat{a}$ can be calculated. This average value $\hat{a}$ can be substituted into each of the aforementioned Equations (2)′ through (4)′ (that is, substituted into the Equations (10)′ through (12)′, below, which are restructured from Equations (7)′ through (9)′, above) to calculate the transmitted scattered radiation intensities $Sc_{n-1}$, $Sc_n$, and $Sc_{n+1}$ for all combinations as again.

$$Sc_{n+1}=G_{n+1}-\hat{a} \cdot P(n+1) \cdot Cp_{n+1} \qquad (10)'$$

$$Sc_n=G_n-\hat{a} \cdot P(n) \cdot Cp_n \qquad (11)'$$

$$Sc_{n-1}=G_{n-1}-\hat{a} \cdot P(n-1) \cdot Cp_{n-1} \qquad (12)'$$

In this way, the intensity estimating portion 44 estimates the transmitted scattered radiation intensities $Sc_{n-1}$, $Sc_n$, and $Sc_{n+1}$ through calculating each using the Equations (10)′ through (12)′, above.

Focusing on the denominators included in the solution to the system of simultaneous equations of Equations (1) and (2)′ through (4)′, as was done with the first example of embodiment, set forth above, is not possible to calculate the transmitted scattered radiation intensities $Sc_{n-1}$, $Sc_n$, and $Sc_{n+1}$, and thus not possible to estimate these transmitted scattered radiation intensities $Sc_{n-1}$, $Sc_n$, and $Sc_{n+1}$ for a combination of three pixels (n−1), n, and (n+1) wherein the denominator of "$\{P(n+1) \cdot Cp_{n+1}+P(n-1) \cdot Cp_{n-1}-2P(n) \cdot Cp_n\}$" is zero. Given this, first the conversion factors $a_n$ for when the denominator is not 0 are each calculated from Equation (6)′, above, and that value is substituted for the transmitted scattered radiation intensities $Sc_n$, not just for the combination of pixels wherein the denominator is not zero, but also for those combinations of pixels wherein the denominator is zero, in Equations (10)′ through (12)′ to perform the calculations.

Summarizing the explanation for solving the system of simultaneous equations, the conversion factors $a_n$ when the denominator "$\{P(n+1) \cdot Cp_{n+1}+P(n-1) \cdot Cp_{n-1}-2P(n) \cdot Cp_n\}$" is not zero are each calculated from Equation (6)′, above, to calculate the average value $\hat{a}$. This average value $\hat{a}$ is substituted into Equations (10)′ through (12)′ for all pixels, to calculate the transmitted scattered radiation intensities $Sc_n$. In this way, the transmitted scattered radiation intensities $Sc_n$ were calculated using Equations (10)' through (12)' for all pixels, including those wherein the denominator "$\{P(n+1) \cdot Cp_{n+1} + P(n-1) \cdot Cp_{n-1} - 2P(n) \cdot Cp_n\}$" is zero, after calculating an average value a' from the conversion factors $a_n$ that were calculated when the denominator "$\{P(n+1) \cdot Cp_{n+1} + P(n-1) \cdot Cp_{n-1} - 2P(n) \cdot Cp_n\}$" was zero; however, there is no limitation thereto.

The transmitted scattered radiation intensities $Sc_{n-1}$, $Sc_n$, and $Sc_{n+1}$ when the denominator "$\{P(n+1) \cdot Cp_{n+1} + P(n-1) \cdot Cp_{n-1} - 2P(n) \cdot Cp_n\}$" is not zero may be calculated prior to calculating the conversion factors $a_n$, the transmitted scattered radiation intensities $Sc_{n-1}$, $Sc_n$, and $Sc_{n+1}$ when the denominator $Sc_{n-1}$, $Sc_n$, and $Sc_{n+1}$ is zero may be calculated through interpolating from the transmitted scattered radiation intensities $Sc_{n-1}$, $Sc_n$, and $Sc_{n+1}$, and the respective calculated transmitted scattered radiation intensities $Sc_{n-1}$, $Sc_n$, and $Sc_{n+1}$ may be substituted into the aforementioned Equations (7)' through (9)', to calculate the conversion factors $a_n$ for both when the denominator "$\{P(n+1) \cdot Cp_{n+1} + P(n-1) \cdot Cp_{n-1} - 2P(n) \cdot Cp_n\}$" is not zero and when the denominator "$\{P(n+1) \cdot Cp_{n+1} + P(n-1) \cdot Cp_{n-1} - 2P(n) \cdot Cp_n\}$" is zero, to calculate the average value $\hat{a}$ of the plurality of sets of conversion factors $a_n$ in the combinations of three pixels (n−1), n, and (n+1) in the center portion of the grid 6 that includes also those places wherein the denominator "$\{P(n+1) \cdot Cp_{n+1} + P(n-1) \cdot Cp_{n-1} - 2P(n) \cdot Cp_n\}$" is zero. Additionally, this average value $\hat{a}$ may be used to recalculate the transmitted scattered radiation intensities $SCn$ $Sc_{n-1}$, $Sc_n$, and $Sc_{n+1}$ through substitution into the aforementioned Equations (10)' through (12)', and the transmitted scattered radiation intensities $Sc_{n-1}$, $Sc_n$, and $Sc_{n+1}$, which have been calculated again, may be used to calculate the deviation ratios Rcs.

As with the first example of embodiment, described above, the transmitted scattered radiation intensities $Sc_{n-1}$, $Sc_n$, and $Sc_{n+1}$, calculated in this way, are used to calculate the deviation ratios Rcs using Equation (13), above, which was described in Step S5 in the first example of embodiment, and then, in Step S6, the actual measured intensities G obtained through actual measurements in the state wherein the actual test subject M is present, the deviation ratios Rcs calculator/interpolated in Step S5, and the direct radiation transmissivities Cp calculated/interpolated in Step S1 are used to solve, in Step S7, the system of simultaneous equations obtained from the aforementioned Equations (1)" through (5)", to estimate the estimated direct radiation intensities $P_{n-1}$, $P_n$, and $P_{n+1}$, and the transmitted scattered radiation intensity $Sc_n(=Sc_{n+1}=Sc_{n-1})$, which is identical to the first example of embodiment, and thus explanations thereof are omitted.

In the x-ray radiography device as set forth in the second example of embodiment, the same operations and effects as in the x-ray radiography device as set forth in the first example of embodiment are produced, and thus explanations of the operations/effects will be omitted.

In the second example of embodiment, the transmitted scattered radiation intensities Sc and the estimated direct radiation intensities P can be estimated easily through solving the system of simultaneous equations obtained from Equations (1)' and (2)' through (4)', above. Additionally, this type of system of simultaneous equations is effective when using a phantom Ph that is near to the actual test subject M (for example, in a case wherein the object is to perform imaging of the torso of a human body, a water cylinder that has transmissivities essentially identical thereto) is used as the test subject M.

The present invention is not limited to the examples of embodiment listed above, but rather can be modified in the embodiment thereof as described below.

(1) While in the examples of embodiment set forth above the explanation used x-rays as an example of the radiation, the present invention can be applied also to radiation other than x-rays (such as, for example, y-rays).

(2) While in the examples of embodiment set forth above the radiography device was structured so as to perform imaging when the test subject was placed on a ceiling plate 1, as illustrated in FIG. 1, the present invention is not limited thereto. For example, the structure may be one wherein imaging is performed after conveying the test subject (which, in this case, an object that is to be inspected is used as a test subject) on a belt, as in a non-destructive inspecting device used in industry, or the like, or may be structured as an x-ray CT device used in medicine, or the like.

Figure 10:
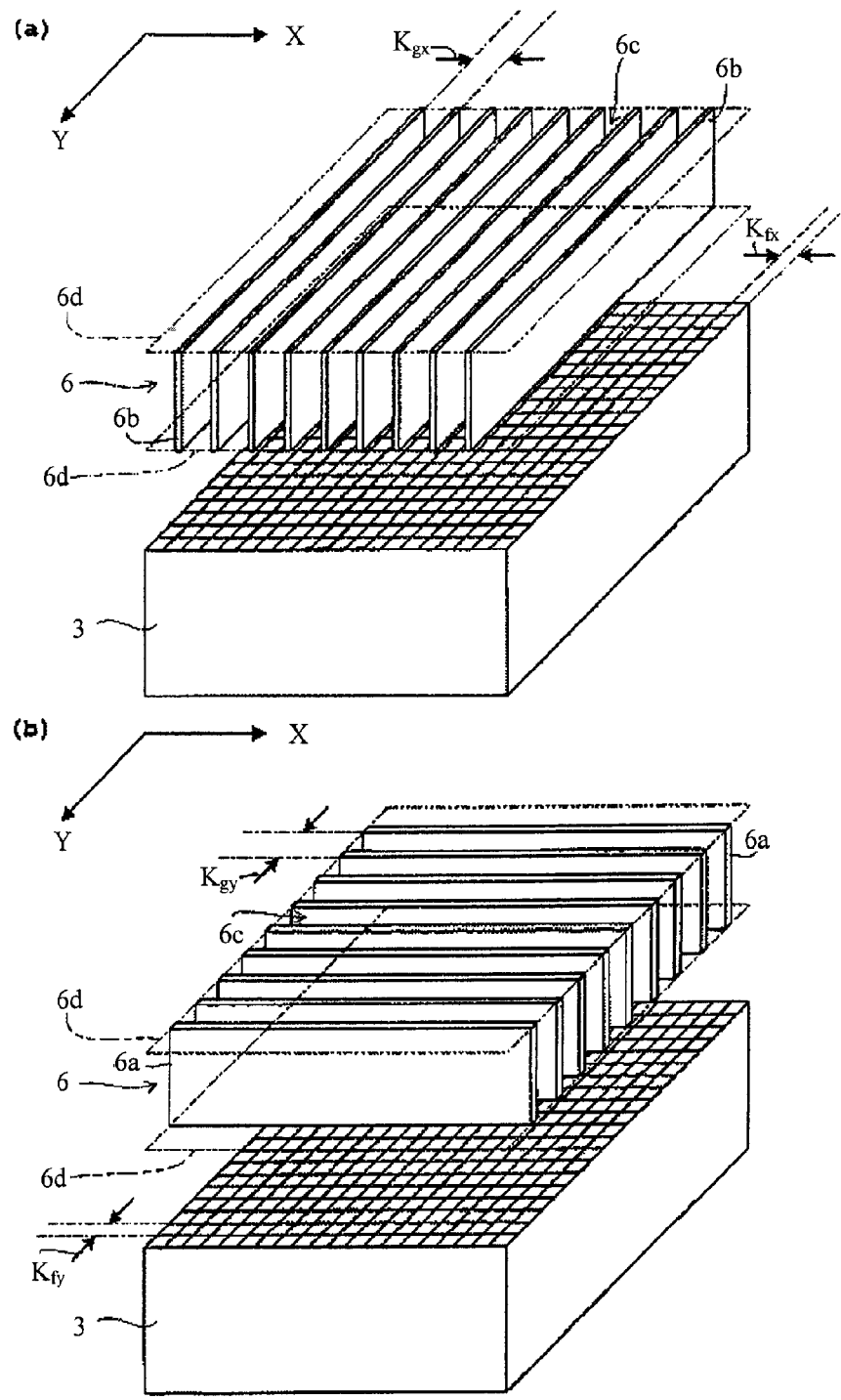
FIGS. 10 (a) and (b) are schematic diagrams of a synchronized grid according to a modified example.

(3) While in the examples of embodiment set forth above an air grid that is a synchronized cross grid was used as the scattered radiation removing means that were typified as a grid, there is no limitation thereto. A grid may be used that is structured with an intermediate material that transmits radiation, such as is typified by x-rays, such as aluminum or an organic material rather than an air gap, and it is not absolutely necessary for the layout direction of the absorbing foil and the middle layers that structure the grid to be parallel to the row direction and column direction of the detecting elements. Furthermore, as illustrated in FIG. 10(*a*) and FIG. 10(*b*), rather than a cross grid, a synchronized grid may be used that is structured so that the layout direction of the absorbing foil is parallel to the row direction and/or the column direction of the detecting elements, and where the spacing between mutually adjacent absorbing foils is an integer multiple of the spacing between mutually adjacent pixels.

(4) In the examples of embodiment set forth above, a method was described wherein deviation ratios for each of the pixels relative to an average value for all of the pixels were calculated for the transmitted scattered radiation intensities Sc using transmitted scattered radiation intensities Sc, wherein the deviation ratios of the transmitted scattered radiation where estimated based on actual measurements in a state wherein the test subject was present. However, as the method for calculating the deviation ratios for the transmitted scattered radiation, there is a method, as a method for calculating the deviation ratios Rcs from actual measurements in a state wherein the test subject is not present, wherein the emitted radiation source is a dummy scattered radiation source (rather than direct radiation) so as to cause direct radiation to be incident into the scattered radiation removing means from a wide angle that is equivalent to the scattered radiation through scanning in two dimensions relative to the grid, and calculating the deviation ratios Rcs through calculating a proportion of the average value of all pixels using a summation value.

(5) In the examples of embodiment set forth above, the number of particular pixels specified by the pixel specifying means (the pixel specifying portion 41 in each of the examples of embodiment) was three; however, there is no limitation to three. The number may be set in accordance with the system of simultaneous equations.

(6) While in the examples of embodiment set forth above, if the absolute value of the denominator included in the solution to the system of simultaneous equations is equal to or less than a particular value, then the pixel specifying means (the pixel specifying portion 41 in each of the examples of embodiment) would not select the particular pixels that would set up that combination of simultaneous equations; however, there is no limitation to the zero value described above for that particular value. A relatively simple case wherein the denominator that is included in the solution for the system of simultaneous equations in either of the examples of embodiment set forth above has a denominator that is included in the estimated direct radiation intensities $P_n$ in calculating/interpolating the direct radiation transmissivities Cp (in Step S2), a denominator that is included in the transmitted scattered radiation intensities Sc for the test subject in estimating/interpolating the intensities (in Step S7), and a denominator $(Cp_{n+1}+Cp_{n-1}-2Cp_n)$ that is included in the estimated direct radiation intensities $P_n$ in calculating/interpolating the direct radiation transmissivities Cp (Step S2), will be explained below.

If, for example, the pixels blocked by the grid foils are defined as n and the pixels that are not blocked are defined as n+1 and n−1, and there is no deformation, or the like, of the foil, then the values for the direct radiation transmissivities Cp at that time can be calculated in advance. If, for example, the width of the pixels is 150 μm, the thickness of the grid to foil is 30 μm, and the middle material is air, then, ignoring the absorption by the grid cover, the following would be true: $Cp_{n+1}=1$, $Cp_{n-1}=1$, and $Cp_n=0.7$. Consequently, the denominator at this time would be $Cp_{n+1}+Cp_{n-1}-2Cp_n=1+1-2\cdot 0.7=0.6$.

On the other hand, the numerator of $P_n$ is $(G_{n+1}+G_{n-1}-2G_n)$, where the statistical fluctuation error can be predicted from the statistical fluctuation error of $G_{n+1}$, $G_{n-1}$, and $G_n$, where the statistical fluctuation error of the $P_n$ that is ultimately obtained is a value that is divided by the value of the denominator. In the example above, this is 0.6 when the foil is in the ideal installation state, but if there is deformation, or the like, in the foil, then that value may be smaller, and the statistical fluctuation error of the numerator, when divided by that statistical fluctuation error, will become large, applying a large error to the average value of the $P_n$, which is calculated later. Consequently, if, for example, the tolerance value is three times that of the ideal situation, then the particular value for the denominator will be 0.2, enabling preventing the calculation of $P_n$ values with high reliability. This approach makes it possible to determine the particular value and then specify the pixels.

As with the case for Step S7, a comparison can be made with the value for the denominator in a proper case, and the particular value can be determined from the value for the tolerance of the statistical fluctuation error of the $P_n$ values that are ultimately obtained. While, in all of the cases above, the particular value was selected based on the tolerance value for the statistical fluctuation error in the value to be calculated, the particular value may instead be determined from another base value.

(7) While in each of the examples of embodiment set forth above the transmitted scattered radiation intensity and the estimated direct radiation intensity were estimated, conversely one or the other may be estimated alone.

(8) As described above, in the present invention "pixel" includes, of course, a single pixel wherein no binning process has been performed, and also includes pixels wherein a plurality of pixels that are handled as a single binned pixel. Consequently, when specifying pixels, or when using specified pixels that have been specified, this may apply to a binned pixel, or may apply to a non-binned pixel.

The invention claimed is:

1. A radiography device for producing a radiation image, comprising: radiation emitting unit emitting radiation; scattered radiation removing device for removing scattered radiation; and radiation detector, wherein a plurality of detecting elements, for detecting radiation, is configured in an array; further comprising:

pixel specifying unit specifying particular pixels from among the various pixels that structure the radiation image;

intensity estimating device estimating scattered radiation intensities at the particular pixels specified by the pixel specifying unit and/or direct radiation intensities of the particular pixels; and intensity interpolating unit interpolating the scattered radiation intensities at pixels that were not specified and/or the direct radiation intensities at pixels that were not specified, based on the scattered radiation intensities and/or direct radiation intensities estimated by the intensity estimating device.

2. A radiography device as set forth in claim 1, wherein:

the scattered radiation removing device is structured such that:

a layout direction of an absorbing layer for absorbing scattered radiation is parallel to the row direction and/or column direction of the detecting elements; and the spacing between mutually adjacent absorbing layers is an integer multiple of the spacing between mutually adjacent pixels.

3. A radiography device as set forth in claim 1, comprising:

transmissivity calculating unit calculating direct radiation transmissivity, which is the transmission ratio of the direct radiation prior to transmission and after transmission through the scattered radiation removing device, calculated through actual measurement in a state wherein no test subject is present.

4. A radiography device as set forth in claim 3, wherein:

the transmissivity calculating units comprise a transmissivity interpolating unit interpolating, for distances before and after discrete distances, direct radiation transmissivities, based on the direct radiation transmissivities calculated by the transmissivity calculating units, calculated for discrete distances between the radiation emitting units, the scattered radiation removing device, and the radiation detector.

5. A radiography device as set forth in claim 3, wherein:

the intensity estimating device estimate radiation intensities for the particular pixels, specified by the pixel specifying unit, based on direct radiation transmissivities calculated by the transmissivity calculating unit and on actual measured intensities, which are the radiation intensities after transmission through the scattered radiation removing means in the actual measurement in a state wherein a test subject is present.

6. A radiography device as set forth in claim 4, wherein:

the intensity estimating device estimate radiation intensities of the particular pixels, specified by the pixel specifying unit, based on the direct radiation transmissivities calculated by the transmissivity calculating unit, the direct radiation transmissivities interpolated by the transmissivity interpolating unit, and actual measured intensities that are radiation intensities after transmission through the scattered radiation removing means of an actual measurement in the state wherein a test subject is present.

7. A radiography device as set forth in claim 5, wherein:

the intensity estimating device, when estimating radiation intensities that are unknown at the particular pixels specified by the pixel specifying unit estimate the radiation intensities by determining the number of particular pixels to be specified by the pixel specifying unit in accordance with the number of knowns for known direct radiation transmissivities and the number of knowns for known actual measured intensities, and then solving a system of simultaneous equations regarding the actual measured intensities, direct radiation transmissivities, and regarding the radiation intensities to be estimated, for each of the particular pixels thus determined.

8. A radiography device as set forth in claim 7, wherein:
when the absolute value of a denominator included in the solution for the system of simultaneous equations is less than a specific value, then rather than selecting the particular pixels that form the combination of the system of simultaneous equations, different particular pixels are combined and selected to be specified, and the intensity specifying means solve the system of simultaneous equations for each specified particular pixel to estimate the radiation intensities, and, for the radiation intensities for those pixels not selected, interpolation is performed by the intensity interpolating means.

9. A radiography device as set forth in claim 7, wherein:
the radiation intensities to be estimated are these transmitted and scattered radiation intensities, which are the scattered radiation intensities after passage through the scattered radiation removing device, and the estimated direct radiation intensities, which are the direct radiation intensities prior to passage through the scattered radiation removing device;
the number of particular pixels to be specified by the pixel specifying unit in accordance with the number of knowns of direct radiation transmissivities and the number of knowns of actual measured intensities is determined to be 3;
a combination of three pixels, comprising an (n−1)th pixel, the nth pixel adjacent thereto, and the (n+1)th pixel adjacent thereto is specified;
when, for each of the three adjacent pixels (n−1), n, and (n+1), the actual measured intensities are defined as $G_{n-1}$, $G_n$, and $G_{n+1}$, the direct radiation transmissivities are defined as $Cp_{n-1}$, $Cp_n$, and $Cp_{n+1}$, the transmitted scattered radiation intensities are defined as $Sc_{n-1}$, $Sc_n$, and $Sc_{n+1}$, and the estimated direct radiation intensities are defined as $P_{n-1}$, $P_n$, and $P_{n+1}$, the intensity estimating means estimate the transmitted scattered radiation intensities or the estimated direct radiation intensities by solving a system of simultaneous equations obtained from an Equation (A) for calculating the transmitted scattered radiation intensities for each pixel through an interpolation calculation on the transmitted scattered radiation intensities of adjacent pixels $$Sc_n = (Sc_{n+1} + Sc_{n-1})/2 \tag{A},$$

a system of simultaneous equations (B-1), (B-2), and (B-3) for each of the three adjacent pixels (n−1), n, and (n+1) after defining the actual measured intensity as being equal to the sum of the transmitted scattered radiation intensity plus the product of the estimated direct radiation intensity times the direct radiation transmissivity $$G_{n+1} = P_{n+1} \cdot Cp_{n+1} + Sc_{n+1} \tag{B-1}$$

$$G_n = P_n \cdot Cp_n + Sc_n \tag{B-2}$$

$$G_{n-1} = P_{n-1} \cdot Cp_{n-1} + Sc_{n-1} \tag{B-3},$$

and an Equation (C) wherein the estimated direct radiation intensity is equal for all three of the adjacent pixels $$P_{n-1} = P_n = P_{n+1} \tag{C}.$$

10. A radiography device as set forth in claim 7, wherein:
the radiation intensities to be estimated are these transmitted and scattered radiation intensities, which are the scattered radiation intensities after passage through the scattered radiation removing device, and the estimated direct radiation intensities, which are the direct radiation intensities prior to passage through the scattered radiation removing device;
the number of particular pixels to be specified by the pixel specifying unit in accordance with the number of knowns of direct radiation transmissivities and the number of knowns of actual measured intensities is determined to be 3;
a combination of three pixels, comprising an (n−1)th pixel, the nth pixel adjacent thereto, and the (n+1)th pixel adjacent thereto is specified;
when, for each of the three adjacent pixels (n−1), n, and (n+1), the actual measured intensities are defined as $G_{n-1}$, $G_n$, and $G_{n+1}$, the direct radiation transmissivities are defined as $Cp_{n-1}$, $Cp_n$, and $Cp_{n+1}$, the transmitted scattered radiation intensities are defined as $Sc_{n-1}$, $Sc_n$, and $Sc_{n+1}$, and the estimated direct radiation intensities are defined as $P_{n-1}$, $P_n$, and $P_{n+1}$, and when the estimated direct radiation intensity is expressed as the product of an estimated direct radiation distribution and a converting factor thereof, where this converting factor is defined as $a_n$, and, for each of three adjacent pixels (n−1), n, and (n+1), the estimated direct radiation distribution is defined as P(n−1), P(n), and P(n+1), the intensity estimating means estimate the transmitted scattered radiation intensities or the estimated direct radiation intensities by solving a system of simultaneous equations obtained from an Equation (A) for calculating the transmitted scattered radiation intensities for each pixel through an interpolation calculation on the transmitted scattered radiation intensities of adjacent pixels $$Sc_n = (Sc_{n+1} + Sc_{n-1})/2 \tag{A},$$

and a system of simultaneous equations (B-1)', (B-2)', and (B-3)' for each of the three adjacent pixels (n−1), n, and (n+1) after defining the actual measured intensity as being equal to the sum of the transmitted scattered radiation intensity plus the product of the estimated direct radiation intensity times the direct radiation transmissivity $$G_{n+1} = a_n \cdot P(n+1) \cdot Cp_{n+1} + Sc_{n+1} \tag{B-1}$$

$$G_n = an \cdot P(n) \cdot Cp_n + Sc_n \tag{B-2}$$

$$G_{n-1} = an \cdot P(n-1) \cdot Cp_{n-1} + Sc_{n-1} \tag{B-3}.$$

11. A radiography device as set forth in claim 5, comprising:
deviation ratio calculating device calculating an average value or a value for each pixel, calculated through a smoothing/interpolation calculation, as a reference intensity for every pixel pertaining to the radiation intensity, using the radiation intensities estimated by the intensity estimating unit based on actual measurements in a state where a test subject is present, to calculate a deviation ratio for each pixel relative to that value; wherein
the deviation ratios calculated by the deviation ratio calculating device are applied to radiography pertaining to a different test subject.

12. A radiography device as set forth in claim 5, comprising:
deviation ratio calculating device for calculating an average value or a value for each pixel, calculated through a smoothing/interpolation calculation, as a reference intensity for every pixel pertaining to the radiation intensity, using the transmitted scattered radiation intensities that are the scattered radiation intensities after transmission through the scattered radiation removing device, estimated through actual measurements using a dummy scattered radiation source in a state wherein no test subject is present, to calculate a deviation ratio for each pixel relative to that value; wherein the deviation ratios calculated by the deviation ratio calculating device are applied to radiography pertaining to a different test subject.

13. A radiography device as set forth in claim 11, wherein:
the deviation ratio calculating device comprise deviation ratio interpolating unit calculating deviation ratios for discrete distances between the radiation emitting unit, the scattered radiation removing device, and the radiation detector, and for performing interpolation on the deviation ratios for distances before and after the discrete distances.

14. A radiography device as set forth in claim 11, wherein the intensity estimating device estimate the radiation intensities at particular pixels specified by the pixel specifying unit based on deviation ratios calculated by the deviation ratio calculating device, direct radiation transmissivities calculated by the transmissivity calculating unit, and actual measured intensities, which are the radiation intensities after transmission through the scattered radiation removing device in an actual measurement in a state wherein another test subject is present.

15. A radiography device as set forth in claim 11, comprising:
the transmissivity calculating unit calculating direct radiation transmissivities for discrete distances between the radiation emitting device, the scattered radiation removing unit, and the radiation detector; and
transmissivity interpolating unit interpolating direct radiation transmissivities for distances before and after the discrete distances based on the direct radiation transmissivities calculated by the transmissivity calculating unit; wherein
the intensity estimating device estimate the radiation intensities at particular pixels specified by the pixel specifying means based on deviation ratios calculated by the deviation ratio calculating device, direct radiation transmissivities interpolated by the transmissivity interpolating unit, and actual measured intensities, which is the radiation intensities after transmission through the scattered radiation removing means in an actual measurement in a state wherein another test subject is present.

16. A radiography device as set forth in claim 13, wherein the intensity estimating device estimate the radiation intensities at particular pixels specified by the pixel specifying unit based on deviation ratios interpolated by the deviation ratio interpolating device, direct radiation transmissivities calculated by the transmissivity calculating unit, and actual measured intensities, which are the radiation intensities after transmission through the scattered radiation removing device in an actual measurement in a state wherein another test subject is present.

17. A radiography device as set forth in claim 13, wherein:
the transmissivity calculating unit calculating direct radiation transmissivities for discrete distances between the radiation emitting device, the scattered radiation removing device, and the radiation detector; and
transmissivity interpolating unit interpolating direct radiation transmissivities for distances before and after the discrete distances based on the direct radiation transmissivities calculated by the transmissivity calculating unit; wherein
the intensity estimating device estimate the radiation intensities at particular pixels specified by the pixel specifying unit based on deviation ratios interpolated by the deviation ratio interpolating device, direct radiation transmissivities interpolated by the transmissivity interpolating unit, and actual measured intensities, which is the radiation intensities after transmission through the scattered radiation removing device in an actual measurement in a state wherein another test subject is present.

18. A radiography device as set forth in claim 14, comprising:
the intensity estimating device, when estimating radiation intensities that are unknown at the particular pixels specified by the pixel specifying unit estimate the radiation intensities by determining the number of particular pixels to be specified by the pixel specifying unit in accordance with the number of knowns for known deviation ratios, the number of knowns for known direct radiation transmissivities, and the number of knowns for known actual measured intensities, and then solving a system of simultaneous equations regarding the actual measured intensities, direct radiation transmissivities, and regarding the radiation intensities to be estimated, for each of the particular pixels thus determined.

19. A radiography device as set forth in claim 18, wherein:
when the absolute value of a denominator included in the solution for the system of simultaneous equations is less than a specific value, then rather than selecting the particular pixels that form the combination of the system of simultaneous equations, different particular pixels are combined and selected to be specified, and the intensity specifying device solve the system of simultaneous equations for each specified particular pixel to estimate the radiation intensities, and, for the radiation intensities for those pixels not selected, interpolation is performed by the intensity interpolating unit.

20. A radiography device as set forth in claim 18, wherein:
the deviation ratios are deviation ratios of the scattered radiation intensities after transmission through the scattered radiation removing device,
the radiation intensities to be estimated are these transmitted and scattered radiation intensities, which are the scattered radiation intensities after being scattered/transmitted by the other test subject and passage through the scattered radiation removing device, and the estimated direct radiation intensities, which are the direct radiation intensities prior to passage through the scattered radiation removing device;
the number of particular pixels to be specified by the pixel specifying unit in accordance with the number of knowns of deviation ratios, the number of knowns of direct radiation transmissivities, and the number of knowns of actual measured intensities is determined to be 3;
a combination of three pixels, comprising an (n−1)th pixel, the nth pixel adjacent thereto, and the (n+1)th pixel adjacent thereto is specified;
when, for each of the three adjacent pixels (n−1), n, and (n+1), the actual measured intensities are defined as $G_{n-1}$, $G_n$, and $G_{n+1}$, the deviation ratios are defined as $Rcs_{n-1}$, $Rcs_n$, and $Rcs_{n+1}$, the direct radiation transmissivities are defined as $Cp_{n-1}$, $Cp_n$, and $Cp_{n+1}$, the transmitted scattered radiation intensities are defined as $Sc_{n-}$ 1, $Sc_n$, and $Sc_{n+1}$, and the estimated direct radiation intensities are defined as $P_{n-1}$, $P_n$, and $P_{n+1}$, the intensity estimating device estimate the transmitted scattered radiation intensities or the estimated direct radiation intensities by solving a system of simultaneous equations obtained from an Equation (A) wherein the transmitted scattered radiation intensities are equal for all three of the adjacent pixels $$Sc_{n-1} = Sc_n = Sc_{n+1} \qquad (A)''$$

a system of simultaneous equations (B-1)', (B-2)', and (B-3)' for each of the three adjacent pixels (n−1), n, and (n+1) after defining the actual measured intensity as being equal to the sum of the product of the transmitted scattered radiation intensity times the deviation ratio plus the product of the estimated direct radiation intensity times the direct radiation transmissivity $$G_{n+1} = P_{n+1} \cdot Cp_{n+1} + Sc_{n+1} \cdot Rcs_{n+1} \qquad (B-1)''$$

$$G_n = P_n \cdot Cp_n + Sc_n \cdot Rcs_n \qquad (B-2)''$$

$$G_{n-1} = P_{n-1} \cdot Cp_{n-1} + Sc_{n-1} \cdot Rcs_{n-1} \qquad (B-3)''$$

and an Equation (C) for calculating the direct radiation intensities for each pixel through an interpolation calculation on the direct radiation intensities of adjacent pixels $$P_n = (P_{n+1} + P_{n-1}) \qquad (C)''$$

21. A radiography device for producing a radiation image, comprising: radiation emitter emitting radiation; scattered radiation removing means for removing scattered radiation; and radiation detector, wherein a plurality of detecting elements, for detecting radiation, is configured in an array; further comprising:

estimated direct radiation intensity calculating device calculating, through averaging or smoothing and interpolating, an estimated direct radiation intensity that is the direct radiation intensity after transmission through the test subject and prior to transmission through the scattered radiation removing device; and transmitted scattered radiation calculating device calculating the transmitted scattered radiation intensity, which is the scattered radiation intensity after transmission through the scattered radiation removing device, based on the estimated direct radiation intensity calculated by the estimated direct radiation intensity calculating device.

22. A radiography device for producing a radiation image, comprising: radiation emitter emitting radiation; scattered radiation remover removing scattered radiation; and radiation detector, wherein a plurality of detecting elements, for detecting radiation, is configured in an array; further comprising:

transmitted scattered radiation calculator calculating through averaging or through smoothing/interpolation transmitted scattered radiation intensities, which are the scattered radiation intensities after transmission through the scattered radiation remover; and direct radiation calculator for calculating direct radiation intensities, which are the direct radiation intensities prior to transmission through the test subject and transmission through the scattered radiation remover, based on the transmitted scattered radiation intensities calculated by the transmitted scattered radiation intensity calculator.

* * * * *